United States Patent
Murua et al.

(10) Patent No.: US 9,309,509 B1
(45) Date of Patent: Apr. 12, 2016

(54) METHODS AND COMPOSITIONS FOR SWEET CORN SUGARY ENHANCER (SEI) GENE

(75) Inventors: Mercedes Murua, Stanton, MN (US); David J Plunkett, Minnetonka, MN (US); Robert Dietrich, Research Triangle Park, NC (US); Molly Dunn, Research Triangle Park, NC (US); Gayle Dace, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 588 days.

(21) Appl. No.: 13/492,359

(22) Filed: Jun. 8, 2012

Related U.S. Application Data

(60) Provisional application No. 61/494,666, filed on Jun. 8, 2011.

(51) Int. Cl.
*C12N 15/00* (2006.01)
*C12Q 1/68* (2006.01)
*A01H 1/04* (2006.01)
*C12N 15/01* (2006.01)

(52) U.S. Cl.
CPC . *C12N 15/01* (2013.01); *A01H 1/04* (2013.01); *C12N 2320/10* (2013.01); *C12Q 1/6827* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

2011/0041204 A1  2/2011  Long

OTHER PUBLICATIONS

Hoisington and Melchinger, 2005, In: Molecular Marker Systems in Plant Breeding and Crop Improvement, Lörz, H., and Wenzel, G., eds, Springer, Berlin, pp. 335-352.*
Tadmor, Y. et al., 1995, Theor. Appl. Genet. 91: 489-494.*
Schultz and Juvik, 2004, Plant Physiology and Biochemistry 42: 457-464.*
Maize GDB—AC217415 locus, pp. 1-5.*
Kaeppler, S, 2010, Modifiers of Endosperm in Sugary1 Maize, USDA grant to University of Wisconsin-Madison, pp. 1-5.*
Databank reference—Genbank Accession #: AC217415: Sequence Title: *Zea mays* chromosome 2 clone ZMMBb-540A10; BBb0540A10; Entry date Oct. 24, 2008.
Databank reference—MaizeGDB Maize B73 RefGen_v2: Chr2: 228025572..231806182.
Gene Hookstra and Asgar Shie, "Sweet Corn Breeding and Genetics Program, Dept. of Agronomy, College of Agricultural and Life Sciences, University of Wisconsin-Madison", International Sweet Corn Dev. Assoc. Dec. 6-7, 2010; from 2010 Report of the Vegtable Breeding Programs Vegetable Breeding Institute, pp. 72-78; Cornell University and University of Wisconsin—Madison.

* cited by examiner

*Primary Examiner* — David T Fox
*Assistant Examiner* — Bratislav Stankovic
(74) *Attorney, Agent, or Firm* — Karen A. Magri

(57) ABSTRACT

The present invention relates to methods and compositions for identifying, selecting and/or producing a corn plant or corn germplasm comprising a corn sugary enhancer gene (SE1) with enhanced sugary trait. A corn plant, part thereof and/or corn germplasm that has been identified, selected and/or produced by any of the methods of the present invention is also provided.

11 Claims, No Drawings

METHODS AND COMPOSITIONS FOR SWEET CORN SUGARY ENHANCER (SEI) GENE

STATEMENT OF PRIORITY

This application claims the benefit, under 35 U.S.C. §119(e), of U.S. Provisional Application Ser. No. 61/494,666, filed Jun. 8, 2011, the entire contents of which are incorporated by reference herein.

FIELD OF THE INVENTION

The present invention relates to compositions and methods for identifying, selecting and producing corn plants with enhanced sugary trait. More particularly, this invention relates to the identification and detection of a deletion associated with the sugary enhancer (se1) gene that is associated with the enhanced sugary trait, as well as the production of plants comprising a deletion associated with the se1 gene that is associated with enhanced sugary trait.

BACKGROUND OF THE INVENTION

Corn (maize) is one of the most diverse grain crops present in nature, comprising a number of different types, which are generally classified by characteristics of their kernel endosperm. The most common types of corn include flint, flour, dent, pop, sweet, waxy and pod. The physical appearance of each kernel type is determined by its endosperm pattern, quality and quantity.

Sweet corn is a corn plant classified as *Zea mays*, var. *rugosa*, and has white, yellow or bi-colored kernels that are sweet when they are in the immature milky stage as a result of having a high sugar content (i.e., sucrose content). Higher levels of sugar or sucrose in the sweet corn kernels result in a lower osmotic potential, causing greater water uptake into the kernels. Sweet corn is typically eaten by human beings as a vegetable, either directly from the maize cob, or by having the sweet kernels removed from the cob, and is a major vegetable crop grown all over the world primarily for fresh consumption, rather than as animal feed or for flour production.

Sweet corn occurs as a spontaneous mutation in field corn and can be the result of naturally-occurring mutations in one or more genes that control conversion of sucrose to starch inside the endosperm of the corn kernel. Unlike field corn varieties, which are intended for livestock and are typically harvested when the kernels are dry and fully mature (at the dent stage), sweet corn is typically picked when it is immature (at the milk stage), and eaten as a vegetable, rather than as a grain. Because the process of maturation involves converting sucrose into starch, sweet corn typically stores poorly and must be eaten in a fresh, canned or frozen manner before the kernels become tough and/or starchy. Following harvest, or if left on the stalk too long, sucrose in standard sweet corn becomes rapidly converted to starch. Kernels can lose as much as 50% of their sucrose at room temperature at around 24 hours after harvest.

Open pollinated (non-hybrid) varieties of white sweet corn started to become widely available in the United States in the 19th century. Two of the most enduring varieties, which are still available today, are Country Gentleman (a Shoepeg corn with small, white kernels in irregular rows) and Stowell's Evergreen. Sweet corn production in the 20th century was influenced by the following key developments: (i) hybridization, which allowed for more uniform maturity, improved quality and disease resistance; and (ii) identification of separate gene mutations responsible for sweetness in corn, and the ability to breed varieties based on these characteristics, for example: su1 (sugary); se1 (sugary enhanced); and sh2 (shrunken-2). There are currently hundreds of varieties of sweet corn, with more varieties continuously being developed.

There are several known genetic mutations that are responsible for the increase in sucrose content of sweet corn. Early varieties were the result of the mutant su1 (sugary-1) allele. Conventional su1 varieties contain about 5-10% sugar by weight.

Varieties of sweet corn that contain the shrunken-2 (sh2) gene typically produce higher than normal levels of sugar and have a longer shelf life, in comparison with conventional sweet corn, and are frequently referred to as supersweet varieties.

One specific gene in sweet corn, the shrunken-2 (sh2) gene, causes the mature corn kernel to dry and shrivel as it matures past the milky stage, which is an undesirable trait for seedling germination, early emergence and plant growth. The endosperm of conventional sh2 sweet corn kernels stores less amounts of starch, and from about 4 to about 10 times more sugar, than conventional su1 sweet corn. This has permitted the long-distance shipping of sweet corn, and has enabled manufacturers to can sweet corn without adding extra sugar or salt to it.

The third gene mutation is the se1 (sugary enhanced-1) allele, which is incorporated in the genome of Everlasting Heritage varieties. Conventional sweet corn varieties with the se1 alleles typically have a longer storage life, and contain from about 12% to about 20% sugar (i.e., a much higher sugar level in comparison with the conventional su1 varieties). The sugary enhanced allele is frequently referred to as the enhanced sugary trait or phenotype.

All of the alleles that are responsible for sweet corn are recessive, so the alleles described above must be in a homozygous state in order for the phenotype that they confer to the sweet corn plant to be observed.

Maize was first classified according to the carbohydrate that is stored in its endosperm. The most distinguishable sugar component that is present in sweet corn is sucrose, which accounts for the vast majority of its sweetness differentiation (Abbott and Cobb, Inc., Plant Protection No. 9600094 (1998)). The reducing free sugars, glucose and fructose, are present in sweet corn in significantly lower levels. These reducing sugars primarily result from the natural hydrolysis of sucrose.

SUMMARY OF THE INVENTION

Compositions and methods for identifying, selecting and producing corn plants having a deletion associated with the se1 gene which is associated with enhanced sugary trait are provided. Corn plants and/or corn germplasms and/or parts thereof having a deletion associated with enhanced sugary trait are also provided.

Thus, one aspect of the present invention is a method of identifying and/or selecting a corn plant or germplasm with enhanced sugary trait, comprising detecting, in said plant or germplasm, the presence of an approximately 0.6 kb deletion within the region defined by positions 229,915,398 and 230,055,870 as set forth in the bacterial artificial chromosome having Maize Genetic and Genomics Database Accession No. AC217415, thereby identifying and/or selecting a corn plant or germplasm that produces kernels with enhanced sugary trait.

Also provided herein is a method of producing a corn plant that produces kernels with enhanced sugary trait, comprising: a) detecting, in corn germplasm, the presence of an approximately 0.6 kb deletion within the region defined by positions 229,915,398 and 230,055,870 as set forth in the bacterial artificial chromosome having Maize Genetic and Genomics Database Accession No. AC217415; and b) producing a plant from said corn germplasm, thereby producing a corn plant that produces kernels with enhanced sugary trait.

In particular embodiments of the methods of this invention, the deletion can comprise, consist essentially of or consist of nucleotides from about position 10,028 to about position 10,642 of the nucleotide sequence of SEQ ID NO:6. This sequence resides on Chromosome 2, Bin 2.09. In the most recent build of the maize physical map (Maize_B73_RefGenv2), this sequence resides within the sequence defined by positions 229972938-229986386.

In some aspects of the methods of this invention, the step of detecting the deletion can comprise, consist essentially of or consist of amplifying a region of the corn genome with a primer pair comprising a first oligonucleotide that hybridizes to the nucleotide sequence of SEQ ID NO:6 at a site 5' to the location of the deletion and a second oligonucleotide that hybridizes to the nucleotide sequence of SEQ ID NO:6 at a site 3' to the location of the deletion to produce an amplification product, wherein an amplification product that differs in base pair size from an amplification product of a control detects the deletion.

In particular embodiments of the method, the step of detecting said deletion can comprise, consist essentially of or consist of amplifying a region of the corn genome with a primer pair comprising a first oligonucleotide comprising the nucleotide sequence of SEQ ID NO:1 (forward primer) and a second oligonucleotide comprising the nucleotide sequence of SEQ ID NO:3 (reverse primer) to produce an amplification product, wherein an amplification product of about 170 base pairs detects the deletion.

In further aspects of this invention, a method is provided of identifying and/or selecting a corn plant or germplasm with enhanced sugary trait, comprising: crossing a first corn plant or germplasm with a second corn plant or germplasm to produce progeny, wherein the first corn plant or germplasm comprises an approximately 0.6 kb deletion within the region defined by positions 229,915,398 and 230,055,870 as set forth in the bacterial artificial chromosome having Maize Genetic and Genomics Database Accession No. AC217415, and selecting from said progeny a corn plant or germplasm that comprises said deletion, thereby identifying and/or selecting a corn plant or germplasm with enhanced sugary trait.

Additionally provided herein is a method of introgressing enhanced sugary trait into a corn plant having a genetic background lacking said trait, comprising: crossing a donor comprising said trait with a recurrent parent that lacks said trait to produce progeny; and repeatedly backcrossing progeny comprising said trait with the recurrent parent, wherein said progeny are identified by detecting the presence, in their genome, of an approximately 0.6 kb deletion within the region defined by positions 229,915,398 and 230,055,870 as set forth in the bacterial artificial chromosome having Maize Genetic and Genomics Database Accession No. AC217415, thereby producing a corn plant with enhanced sugary trait, and thereby introgressing said trait into a corn plant having a genetic background lacking said trait.

The present invention also provides a corn plant or germplasm having in its genome a marker associated with enhanced sugary trait wherein said marker is an approximately 0.6 kb deletion within the region defined by positions 229,915,398 and 230,055,870 as set forth in the bacterial artificial chromosome having Maize Genetic and Genomics Database Accession No. AC217415, identified, produced or selected by any of the methods of this invention and/or a cell, seed or tissue culture thereof.

Furthermore, the present invention provides a non-naturally occurring corn plant or germplasm having in its genome a marker associated with enhanced sugary trait, wherein said marker is an approximately 0.6 kb deletion within the region defined by positions 229,915,398 and 230,055,870 as set forth in the bacterial artificial chromosome having Maize Genetic and Genomics Database Accession No. AC217415. Also included herewith is a seed produced by a corn plant of this invention.

An additional aspect of this invention is an introgressed corn plant or germplasm produced according any one of the methods of this invention, and/or a cell, seed, or tissue culture thereof.

The present invention also provides a primer pair for amplification of a nucleic acid sample from a corn plant or germplasm to produce an amplification product comprising a deletion associated with enhanced sugary trait as described herein. In some embodiments the primer pair of this invention can comprise, consist essentially of or consist of a first oligonucleotide comprising the nucleotide sequence of SEQ ID NO:1 and a second oligonucleotide comprising the nucleotide sequence of SEQ ID NO:3.

These and other aspects of the invention are set forth in more detail in the description of the invention below.

DETAILED DESCRIPTION OF THE INVENTION

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art.

All patents, patent publications, non-patent publications and sequences referenced herein are incorporated by reference in their entireties.

The present invention provides a method of identifying and/or selecting a corn plant or germplasm with enhanced sugary trait, comprising detecting, in said plant or germplasm, the presence of an approximately 0.6 kb deletion within the region defined by positions 229,915,398 and 230,055,870 as set forth in the bacterial artificial chromosome having Maize Genetic and Genomics Database Accession No. AC217415, thereby identifying and/or selecting a corn plant or germplasm with enhanced sugary trait.

Additionally provided herein is a method of producing a corn plant with enhanced sugary trait, comprising: a) detecting, in corn germplasm, the presence of an approximately 0.6 kb deletion within the region defined by positions 229,915, 398 and 230,055,870 as set forth in the bacterial artificial chromosome having Maize Genetic and Genomics Database Accession No. AC217415; and b) producing a plant from said corn germplasm, thereby producing a corn plant with enhanced sugary trait.

The deletion described herein is in or is closely linked to the sugary enhanced (se1) gene and the deletion can comprise, consist essentially of or consist of nucleotides from about position 10,028 to about position 10,642 of the nucleotide sequence of SEQ ID NO:6. In some embodiments, the nucleotides that are deleted comprise, consist essentially of or consist of the nucleotide sequence of SEQ ID NO:4. In a corn plant or germplasm with enhanced sugary trait, the nucleotide sequence of SEQ ID NO:5 can be present, which defines the nucleotide sequence that results from deletion of the approximately 0.6 kb of SEQ ID NO:4. Thus, in some embodiments, detection of the nucleotide sequence of SEQ ID NO:5 and/or a substantial portion thereof that would not be detectable in a plant or germplasm lacking this deletion allows for the identification of a corn plant or germplasm as having enhanced sugary trait.

In further embodiments, detecting the deletion of this invention can comprise amplifying a region of the corn genome with a primer pair comprising a first oligonucleotide that hybridizes to the nucleotide sequence of SEQ ID NO:6 at a site 5' to the location of the deletion and a second oligonucleotide that hybridizes to the nucleotide sequence of SEQ ID NO:6 at a site 3' to the location of the deletion to produce an amplification product, wherein an amplification product that differs in base pair size from an amplification product of a control corn plant (e.g., a corn plant lacking the deletion of this invention) detects the deletion. With the nucleotide sequence of the deletion described herein, one of ordinary skill in the art would be able to readily identify and produce a primer pair as described herein for use in an amplification reaction to determine the presence or absence of the deletion of this invention.

In particular embodiments of this invention, detection of the deletion described herein can comprise amplifying a region of the corn genome with a primer pair comprising a first oligonucleotide comprising the nucleotide sequence of SEQ ID NO:1 (forward primer) and a second oligonucleotide comprising the nucleotide sequence of SEQ ID NO:3 (reverse primer) to produce an amplification product, wherein an amplification product of about 170 base pairs (e.g., 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189 or 190 base pairs) detects the deletion. No amplification product of about 170 base pairs, or an amplification product of about 110 base pairs resulting from an amplification reaction employing the oligonucleotides of SEQ ID NO:1 and SEQ ID NO:3 identifies a corn plant or germplasm lacking the deletion of this invention.

The present invention additionally provides a method of identifying and/or selecting a corn plant or germplasm with enhanced sugary trait, comprising: crossing a first corn plant or germplasm with a second corn plant or germplasm to produce progeny, wherein the first corn plant or germplasm comprises an approximately 0.6 kb deletion within the region defined by positions 229,915,398 and 230,055,870 as set forth in the bacterial artificial chromosome having Maize Genetic and Genomics Database Accession No. AC217415, and selecting from said progeny a corn plant or germplasm that comprises said deletion, thereby identifying and/or selecting a corn plant or germplasm with enhanced sugary trait.

In some embodiments of the method described above, the genome of the second plant or germplasm can be at least 95% identical to that of an elite variety of corn and in some embodiments, the genome of the second plant or germplasm is of an elite variety of corn.

Furthermore, the present invention provides a method of introgressing enhanced sugary trait into a corn plant having a genetic background lacking said trait, comprising: crossing a donor comprising said trait with a recurrent parent that lacks said trait to produce progeny; and repeatedly backcrossing progeny comprising said trait with the recurrent parent, wherein said progeny are identified by detecting the presence, in their genome, of an approximately 0.6 kb deletion within the region defined by positions 229,915,398 and 230,055,870 as set forth in the bacterial artificial chromosome having Maize Genetic and Genomics Database Accession No. AC217415, thereby producing a corn plant with enhanced sugary trait, and thereby introgressing said trait into a corn plant having a genetic background lacking said trait.

In some embodiments of the method described above, the genome of the corn plant comprising the enhanced sugary trait can be at least 95% identical to that of a recurrent parent. In some embodiments, the genome of the recurrent parent plant or germplasm can be at least 95% identical to that of an elite variety of corn and in some embodiments, the recurrent parent is of an elite variety of corn.

The present invention further provides a corn plant or germplasm having in its genome a marker associated with enhanced sugary trait, wherein said marker is an approximately 0.6 kb deletion within the region defined by positions 229,915,398 and 230,055,870 as set forth in the bacterial artificial chromosome having Maize Genetic and Genomics Database Accession No. AC217415, identified, produced or selected by a method of this invention and/or a cell, seed or tissue culture thereof.

Additionally provided herein is a non-naturally occurring corn plant or germplasm having in its genome a marker associated with enhanced sugary trait, wherein said marker is an approximately 0.6 kb deletion within the region defined by positions 229,915,398 and 230,055,870 as set forth in the bacterial artificial chromosome having Maize Genetic and Genomics Database Accession No. AC217415.

In some embodiments of a corn plant or germplasm of this invention, the genome of said corn plant or germplasm can be at least 95% identical to that of an elite variety of corn. In further embodiments, a corn plant or germplasm of this invention, can be derived from crossing an elite variety of corn with an exotic variety of corn.

Additionally provided herein is a seed produced by a corn plant of this invention.

Further embodiments of this invention include an introgressed corn plant or germplasm produced according to any of the methods of this invention, and/or a cell, seed, or tissue culture thereof.

Also provided herein is a primer pair for amplification of nucleic acid in a sample from a corn plant or germplasm to produce an amplification product comprising a deletion associated with enhanced sugary trait. In some embodiments, the primer pair can comprise, consist essentially of or consist of a first oligonucleotide comprising the nucleotide sequence of SEQ ID NO:1 and a second oligonucleotide comprising the nucleotide sequence of SEQ ID NO:3, In some embodiments, the primer pair can comprise, consist essentially of or consist of a first oligonucleotide comprising the nucleotide sequence of SEQ ID NO:2 and a second oligonucleotide comprising the nucleotide sequence of SEQ ID NO:3.

DEFINITIONS

Although the following terms are believed to be well understood by one of ordinary skill in the art, the following definitions are set forth to facilitate understanding of the presently disclosed subject matter.

As used herein, the terms "a" or "an" or "the" may refer to one or more than one. For example, "a" marker (e.g., SNP) can mean one marker or a plurality of markers (e.g., 2, 3, 4, 5, 6, 7, 8, 9, 10 and the like).

As used herein, the term "and/or" refers to and encompasses any and all possible combinations of one or more of the associated listed items, as well as the lack of combinations when interpreted in the alternative ("or").

As used herein, the term "about," when used in reference to a measurable value such as length of a nucleotide sequence, number of nucleotides, an amount of mass, dose, time, temperature, and the like, is meant to encompass variations of 20%, 10%, 5%, 1%, 0.5%, or even 0.1% of the specified amount.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the term "enhanced sugary trait" means plants displaying the effects of the sugary enhancer (se1) mutant gene. The sugary enhancer gene has been characterized phenotypically as the exact nucleic acid sequence responsible for the phenotype has not yet been identified. The sugary enhancer (se1) mutant gene is a recessive modifier of the sugary-1 (su1) gene mutation. (Shultz et al. "Current Models for Starch Synthesis and the Sugary Enhancer 1 (se 1) Mutation in *Zea maysi*"). The sugary enhancer (se1) gene locus is situated on the long arm of chromosome 2 in sweet corn. When homozygous, the sugary enhancer (se1) allele increases total sugar in conventional sugary-1 (su1) variety corn kernels to levels that are comparable to those in shrunken-2 (sh2) variety corn kernels, and without a reduction in phytoglycogen content.

The effects of the sugary enhancer (se1) gene are corn kernel elevated total sugars, lighter color, and slow dry down, and were originally observed in an inbred corn line designated as IL1677a. It was only later that these effects were attributed to the sugary enhancer (se1) gene. (Brink "Identity and Sources of a Sugary Enhancer Gene Located on the Long Arm of Chromosome 4 in Maize" *J. Heredity* 82:176 (1991)).

The sugary enhancer (se1) gene confers higher moisture content to sweet corn kernels during postharvest periods of time and also maintains relatively increased levels of phytoglycogen during this time. Additional benefits of this gene are reduced kernel pericarp levels (which can be observed as a more finely wrinkled pericarp), rendering corn kernels with an improved tenderness, and elevated levels of the sugar maltose. (Ferguson et al. "Genetics of Sugary Enhancer (Se), an Independent Modifier of Sweet Corn (Su)" *J. Heredity* 69(6):377-380 (1978)).

When both the sugary enhancer (se1) gene and the sugary (su1) gene are homozygous, the sugary enhancer (se1) gene very advantageously confers from about 1.5 to about 2 times more sucrose to corn kernels at their peak harvest maturity in comparison with sugary (su1) gene mutant corn kernels.

As used herein, the term "allele" refers to one of two or more different nucleotides or nucleotide sequences that occur at a specific locus.

A "locus" is a position on a chromosome where a gene or marker or allele is located. In some embodiments, a locus may encompass one or more nucleotides.

A marker is "associated with" a trait when it is linked to it and/or statistically correlated with the trait and when the presence of the marker is an indicator of whether and/or to what extent the desired trait or trait form will occur in a plant/germplasm comprising the marker.

As used herein, the terms "backcross" and "backcrossing" refer to the process whereby a progeny plant is crossed back to one of its parents one or more times (e.g., 1, 2, 3, 4, 5, 6, 7, 8, etc.). In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example*, in TECHNIQUES ET UTILISATIONS DES MARQUEURS MOLECULAIRES LES COLLOQUES, Vol. 72, pp. 45-56 (1995); and Openshaw et al., *Marker-assisted Selection in Backcross Breeding*, in PROCEEDINGS OF THE SYMPOSIUM "ANALYSIS OF MOLECULAR MARKER DATA," pp. 41-43 (1994). The initial cross gives rise to the F1 generation. The term "BC1" refers to the second use of the recurrent parent, "BC2" refers to the third use of the recurrent parent, and so on.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "cultivar" and "variety" refer to a group of similar plants that by structural or genetic features and/or performance can be distinguished from other cultivars/varieties within the same species.

As used herein, the terms "elite" and/or "elite line" refer to any line that is substantially homozygous and has resulted from breeding and selection for desirable agronomic performance.

A "genetic map" is a description of genetic linkage relationships among loci on one or more chromosomes within a given species, generally depicted in a diagrammatic or tabular form. For each genetic map, distances between loci are measured by the recombination frequencies between them. Recombination between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, as well as plant parts, such as leaves, stems, pollen, or cells that can be cultured into a whole plant.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "inbred" refers to a substantially homozygous plant or variety. The term may refer to a plant or plant variety that is substantially homozygous throughout the entire genome or that is substantially homozygous with respect to a portion of the genome that is of particular interest.

As used herein, the term "indel" refers to an insertion or deletion in a pair of nucleotide sequences, wherein a first sequence may be referred to as having an insertion relative to a second sequence or the second sequence may be referred to as having a deletion relative to the first sequence.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. Offspring comprising the desired allele can be repeatedly backcrossed to a line having a desired genetic background and selected for the desired allele, with the result being that the desired allele becomes fixed in the desired genetic background. For example, a marker associated with enhanced sugary trait (e.g., the se1 deletion described herein) may be introgressed from a donor into a recurrent parent lacking enhanced sugary trait. The resulting offspring could then be repeatedly backcrossed and selected until the progeny possess the marker for enhanced sugary trait in the recurrent parent background.

As used herein, the term "linkage" refers to the degree with which one marker locus is associated with another marker locus. The linkage relationship between a molecular marker and a phenotype may be given as a "probability" or "adjusted probability." Linkage can be expressed as a desired limit or range. For example, in some embodiments, any marker is linked (genetically and physically) to any other marker when the markers segregate from each other in the next generation less than 50% of the time, less than 25% of the time, less than 20% of the time, less than 15% of the time, less than 10% of the time, less than 5% of the time, less than 4% of the time, less than 3% of the time, less than 2% of the time, or less than 1% of the time. Thus, in some embodiments, two loci are linked when they are separated by less than about 50, 40, 30, 25, 20, 15, 10, 5, 4, 3, 2, 1, or 0.5 map units or centiMorgans (cM).

As used herein, the phrase "linkage group" refers to all of the genes or genetic traits that are located on the same chromosome. Within the linkage group, those loci that are close enough together can exhibit linkage in genetic crosses. Since the probability of crossover increases with the physical distance between loci on a chromosome, loci for which the locations are far removed from each other within a linkage group might not exhibit any detectable linkage in direct genetic tests. The term "linkage group" is mostly used to refer to genetic loci that exhibit linked behavior in genetic systems where chromosomal assignments have not yet been made. Thus, the term "linkage group" is synonymous with the physical entity of a chromosome, although one of ordinary skill in the art will understand that a linkage group can also be defined as corresponding to a region (i.e., less than the entirety) of a given chromosome.

A centimorgan ("cM") or a genetic map unit (m.u.) is a unit of measure of recombination frequency and is defined as the distance between genes for which one product of meiosis in 100 is recombinant. One cM is equal to a 1% chance that a marker at one genetic locus will be separated from a marker at a second locus due to crossing over in a single generation. Thus, a recombinant frequency (RF) of 1% is equivalent to 1 m.u.

As used herein, the term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and, by definition, are separated by less than 50 cM on the same chromosome). As used herein, linkage can be between two markers, or alternatively between a marker and a phenotype/trait. A marker locus can be "associated with" (linked to) a trait, e.g., enhanced sugary trait. The degree of linkage of a genetic marker to a phenotypic trait is measured, e.g., as a statistical probability of co-segregation of that genetic marker with the phenotype.

Linkage disequilibrium is most commonly assessed using the measure $r^2$, which is calculated using the formula described by Hill and Robertson (*Theor. Appl. Genet.* 38:226 (1968)). When $r^2=1$, complete linkage disequilibrium exists between the two marker loci, meaning that the markers have not been separated by recombination and have the same allele frequency. Values for $r^2$ above ⅓ indicate sufficiently strong linkage disequilibrium to be useful for mapping. Ardlie et al. (*Nature Reviews Genetics* 3:299 (2002)). Hence, alleles are in linkage disequilibrium when $r^2$ values between pairwise marker loci are greater than or equal to about 0.33, 0.4, 0.5, 0.6, 0.7, 0.8, 0.9, or 1.0.

As used herein, the term "linkage equilibrium" describes a situation where two markers independently segregate, i.e., sort among progeny randomly. Markers that show linkage equilibrium are considered unlinked (whether or not they lie on the same chromosome).

As used herein, the terms "marker" and "genetic marker" are used interchangeably to refer to a nucleotide and/or a nucleotide sequence that has been associated with a phenotype and/or trait. A marker may be, but is not limited to, a deletion, an insertion, a SNP allele and/or combination of SNP alleles (haplotype) (Brookes, *Gene* 234:177 (1993)), a gene, a chromosome interval, a restriction fragment length polymorphism (RFLP), a simple sequence repeat (SSR), a random amplified polymorphic DNA (RAPD), a cleaved amplified polymorphic sequence (CAPS) (Rafalski and Tingey, *Trends in Genetics* 9:275 (1993)), an amplified fragment length polymorphism (AFLP) (Vos et al., *Nucleic Acids Res.* 23:4407 (1995)), a sequence-characterized amplified region (SCAR) (Paran and Michelmore, *Theor. Appl. Genet.*

85:985 (1993)), a sequence-tagged site (STS) (Onozaki et al., *Euphytica* 138:255 (2004)), a single-stranded conformation polymorphism (SSCP) (Orita et al., *Proc. Natl. Acad. Sci. USA* 86:2766 (1989)), an inter-simple sequence repeat (ISSR) (Blair et al., *Theor. Appl. Genet.* 98:780 (1999)), an inter-retrotransposon amplified polymorphism (IRAP), a retrotransposon-microsatellite amplified polymorphism (REMAP) (Kalendar et al., *Theor. Appl. Genet.* 98:704 (1999)), an isozyme marker, an RNA cleavage product (such as a Lynx tag) or any combination of the markers described herein. A marker may be present in genomic or expressed nucleic acids (e.g., ESTs).

Markers corresponding to genetic polymorphisms between members of a population can be detected by methods well-established in the art. These include, e.g., nucleic acid sequencing, hybridization methods, amplification methods (e.g., PCR-based sequence specific amplification methods), detection of a deletion, detection of an insertion, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), and/or detection of amplified fragment length polymorphisms (AFLPs). Well established methods are also known for detecting expressed sequence tags (ESTs) and SSR markers derived from EST sequences and randomly amplified polymorphic DNA (RAPD).

Accordingly, in some embodiments of this invention, a marker corresponds to an amplification product generated by amplifying a corn genomic nucleic acid with two oligonucleotide primers, for example, by the polymerase chain reaction (PCR). As used herein, the phrase "corresponds to an amplification product" in the context of a marker refers to a marker that has a nucleotide sequence that is the same (allowing for mutations introduced by the amplification reaction itself) as an amplification product that is generated by amplifying corn genomic DNA with a particular set of primers. In some embodiments, the amplifying is by PCR, and the primers are PCR primers that are designed to hybridize to opposite strands of the corn genomic DNA in order to amplify a corn genomic DNA sequence present between the sequences to which the PCR primers hybridize in the corn genomic DNA. In other embodiments, a marker that "corresponds to" an amplified fragment is a marker that has the same sequence of one of the strands of the amplified fragment.

A "marker allele," also described as an "allele of a marker locus," can refer to one of a plurality of polymorphic nucleotide sequences found at a marker locus in a population that is polymorphic for the marker locus.

"Marker-assisted selection" (MAS) is a process by which phenotypes are selected based on marker genotypes. Marker assisted selection includes the use of marker genotypes for identifying plants for inclusion in and/or removal from a breeding program or planting.

As used herein, the terms "marker locus" and "marker loci" refer to a specific chromosome location or locations in the genome of an organism where a specific marker or markers can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

As used herein, the terms "marker probe" and "probe" refer to a nucleotide sequence or nucleic acid molecule that can be used to detect the presence of one or more particular alleles within a marker locus (e.g., a nucleic acid probe that is complementary to all of or a portion of the marker or marker locus, through nucleic acid hybridization). Marker probes comprising about 8, 10, 15, 20, 30, 40, 50, 60, 70, 80, 90, 100 or more contiguous nucleotides may be used for nucleic acid hybridization. Alternatively, in some aspects, a marker probe refers to a probe of any type that is able to distinguish (i.e., genotype) the particular allele that is present at a marker locus. In some embodiments, the term "probe" refers to a single-stranded oligonucleotide sequence that will form a hydrogen-bonded duplex with a complementary sequence in a target nucleic acid sequence analyte or its cDNA derivative.

As used herein, the term "molecular marker" may be used to refer to a genetic marker, as defined above, or an encoded product thereof (e.g., a protein) used as a point of reference when identifying a linked locus. A molecular marker can be derived from genomic nucleotide sequences or from expressed nucleotide sequences (e.g., from a spliced RNA, a cDNA, etc.). The term also refers to nucleotide sequences complementary to or flanking the marker sequences, such as nucleotide sequences used as probes and/or primers capable of amplifying the marker sequence. Nucleotide sequences are "complementary" when they specifically hybridize in solution, e.g., according to Watson-Crick base pairing rules. Some of markers can also be referred to as hybridization markers when located on an indel region. This is because the insertion or deletion region is, by definition, a polymorphism vis-à-vis a plant without the insertion or deletion. Thus, the marker need only indicate whether the indel region is present or absent. Any suitable marker detection technology may be used to identify such a hybridization marker.

As used herein, the term "non-naturally occurring corn plant or germplasm" refers to a corn plant or germplasm that does not naturally exist in nature. A "non-naturally occurring corn plant or germplasm" may be produced by any method known in the art, including, but not limited to, transforming a corn plant or germplasm, transfecting a corn plant or germplasm and crossing a naturally occurring variety of corn with a non-naturally occurring variety of corn. In some embodiments, a "non-naturally occurring corn plant or germplasm" may comprise one of more heterologous nucleotide sequences. In some embodiments, a "non-naturally occurring corn plant or germplasm" may comprise one or more non-naturally occurring copies of a naturally occurring nucleotide sequence (i.e., extraneous copies of a gene that naturally occurs in corn) or may lack a naturally occurring nucleotide sequence. In some embodiments, a "non-naturally occurring corn plant or germplasm" may comprise a non-natural combination of two or more naturally occurring nucleotide sequences (i.e., two or more naturally occurring genes that do not naturally occur in the same corn).

As used herein, the term "primer" refers to an oligonucleotide which is capable of annealing to a nucleic acid target and serving as a point of initiation of DNA synthesis when placed under conditions in which synthesis of a primer extension product is induced (e.g., in the presence of nucleotides and an agent for polymerization such as DNA polymerase and at a suitable temperature and pH). A primer (in some embodiments an extension primer and in some embodiments an amplification primer) is in some embodiments single stranded for maximum efficiency in extension and/or amplification. In some embodiments, the primer is an oligodeoxyribonucleotide. A primer is typically sufficiently long to prime the synthesis of extension and/or amplification products in the presence of the agent for polymerization. The minimum length of a primer can depend on many factors, including, but not limited to temperature and composition (A/T vs. G/C content) of the primer.

In the context of amplification primers, these are typically provided as a pair of bi-directional primers (i.e., a primer pair) consisting of one forward and one reverse primer or provided as a pair of forward primers as commonly used in the art of DNA amplification such as in PCR amplification.

As such, it will be understood that the term "primer," as used herein, can refer to more than one primer, particularly in the case where there is some ambiguity in the information regarding the terminal sequence(s) of the target region to be amplified. Hence, a "primer" can include a collection of primer oligonucleotides containing sequences representing the possible variations in the sequence or includes nucleotides which allow a typical base pairing.

Primers can be prepared by any suitable method. Methods for preparing oligonucleotides of specific sequence are known in the art, and include, for example, cloning and restriction of appropriate sequences and direct chemical synthesis. Chemical synthesis methods can include, for example, the phospho di- or tri-ester method, the diethylphosphoramidate method and the solid support method disclosed in U.S. Pat. No. 4,458,066.

Primers can be labeled, if desired, by incorporating detectable moieties by for instance spectroscopic, fluorescence, photochemical, biochemical, immunochemical, or chemical moieties.

The PCR method is well described in handbooks and known to the skilled person. After amplification by PCR, target polynucleotides can be detected by hybridization with a probe polynucleotide which forms a stable hybrid with that of the target sequence under stringent to moderately stringent hybridization and wash conditions. If it is expected that the probes are essentially completely complementary (i.e., about 99% or greater) to the target sequence, stringent conditions can be used. If some mismatching is expected, for example if variant strains are expected with the result that the probe will not be completely complementary, the stringency of hybridization can be reduced. In some embodiments, conditions are chosen to rule out non-specific/adventitious binding. Conditions that affect hybridization, and that select against non-specific binding are known in the art, and are described in, for example, Sambrook & Russell (2001). *Molecular Cloning: A Laboratory Manual, Third Edition,* Cold Spring Harbor Laboratory Press, Cold Spring Harbor, N.Y., United States of America. Generally, lower salt concentration and higher temperature hybridization and/or washes increase the stringency of hybridization conditions.

Different nucleotide sequences or polypeptide sequences having homology are referred to herein as "homologues." The term homologue includes homologous sequences from the same and other species and orthologous sequences from the same and other species. "Homology" refers to the level of similarity between two or more nucleotide sequences and/or amino acid sequences in terms of percent of positional identity (i.e., sequence similarity or identity). Homology also refers to the concept of similar functional properties among different nucleic acids, amino acids, and/or proteins.

As used herein, the phrase "nucleotide sequence homology" refers to the presence of homology between two polynucleotides. Polynucleotides have "homologous" sequences if the sequence of nucleotides in the two sequences is the same when aligned for maximum correspondence. The "percentage of sequence homology" for polynucleotides, such as 50, 55, 60, 65, 70, 75, 80, 85, 90, 95, 96, 97, 98, 99 or 100 percent sequence homology, can be determined by comparing two optimally aligned sequences over a comparison window (e.g., about 20-200 contiguous nucleotides), wherein the portion of the polynucleotide sequence in the comparison window can include additions or deletions (i.e., gaps) as compared to a reference sequence for optimal alignment of the two sequences. Optimal alignment of sequences for comparison can be conducted by computerized implementations of known algorithms, or by visual inspection. Readily available sequence comparison and multiple sequence alignment algorithms are, respectively, the Basic Local Alignment Search Tool (BLAST®; Altschul et al. (1990) *J Mol Biol* 215:403-10; Altschul et al. (1997) *Nucleic Acids Res* 25:3389-3402) and ClustalX (Chenna et al. (2003) *Nucleic Acids Res* 31:3497-3500) programs, both available on the Internet. Other suitable programs include, but are not limited to, GAP, BestFit, PlotSimilarity, and FASTA, which are part of the Accelrys GCG Package available from Accelrys Software, Inc. of San Diego, Calif., United States of America.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing; Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "substantially identical" or "corresponding to" means that two nucleotide sequences have at least 50%, 60%, 70%, 75%, 80%, 85%, 90% or 95% sequence identity. In some embodiments, the two nucleotide sequences can have at least 85%, 90%, 95%, 96%, 97%, 98%, 99% or 100% sequence identity.

An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). In some embodiments, "percent identity" can refer to the percentage of identical amino acids in an amino acid sequence.

Optimal alignment of sequences for aligning a comparison window is well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., Burlington, Mass.). The comparison of one or more polynucleotide sequences may be to a full-length polynucleotide sequence or a portion thereof, or to a longer polynucleotide sequence. For purposes of this invention "percent identity" may also be determined using BLAST® X version 2.0 for translated nucleotide sequences and BLAST® N version 2.0 for polynucleotide sequences.

The percent of sequence identity can be determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, *J Mol. Biol.* 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (*Adv. Appl. Math.*, 2:482-489, 1981, Smith et al., *Nucleic Acids Res.* 11:2205-2220, 1983).

Useful methods for determining sequence identity are also disclosed in *Guide to Huge Computers* (Martin J. Bishop, ed., Academic Press, San Diego (1994)), and Carillo et al. (*Applied Math* 48:1073 (1988)). More particularly, preferred computer programs for determining sequence identity include but are not limited to the Basic Local Alignment Search Tool (BLAST®) programs which are publicly available from National Center Biotechnology Information (NCBI) at the National Library of Medicine, National Institutes of Health, Bethesda, Md. 20894; see BLAST® Manual, Altschul et al., NCBI, NLM, NIH; (Altschul et al., *J. Mol. Biol.* 215:403-410 (1990)); version 2.0 or higher of BLAST® programs allows the introduction of gaps (deletions and insertions) into alignments; for peptide sequence BLAST® X can be used to determine sequence identity; and for polynucleotide sequence BLAST® N can be used to determine sequence identity.

As used herein, the terms "phenotype," "phenotypic trait" or "trait" refer to one or more traits of an organism. The phenotype can be observable to the naked eye, or by any other means of evaluation known in the art, e.g., microscopy, biochemical analysis, and/or an electromechanical assay. In some cases, a phenotype is directly controlled by a single gene or genetic locus, i.e., a "single gene trait." In other cases, a phenotype is the result of several genes.

As used herein, the term "polymorphism" refers to a variation in the nucleotide sequence at a locus, where the variation is too common to be due merely to a spontaneous mutation. A polymorphism can be a single nucleotide polymorphism (SNP), or an insertion/deletion polymorphism, also referred to herein as an "indel." Additionally, the variation can be in a transcriptional profile or a methylation pattern. The polymorphic site or sites of a nucleotide sequence can be determined by comparing the nucleotide sequences at one or more loci in two or more germplasm entries.

As used herein, the term "plant" can refer to a whole plant, any part thereof, or a cell or tissue culture derived from a plant. Thus, the term "plant" can refer to a whole plant, a plant component or a plant organ (e.g., leaves, stems, roots, etc.), a plant tissue, a seeds and/or a plant cell. A plant cell is a cell of a plant, taken from a plant, or derived through culture from a cell taken from a plant.

As used herein, the term "plant part" includes but is not limited to embryos, pollen, seeds, leaves, flowers (including but not limited to anthers, ovules and the like), fruit, stems or branches, roots, root tips, cells including cells that are intact in plants and/or parts of plants, protoplasts, plant cell tissue cultures, plant calli, plant clumps, and the like. Thus, a plant part includes corn tissue cultures from which corn plants can be regenerated. Further, as used herein, "plant cell" refers to a structural and physiological unit of the plant, which comprises a cell wall and also may refer to a protoplast. A plant cell of the present invention can be in the form of an isolated single cell or can be a cultured cell or can be a part of a higher-organized unit such as, for example, a plant tissue or a plant organ.

As used herein, the term "population" refers to a genetically heterogeneous collection of plants sharing a common genetic derivation.

As used herein, the terms "progeny," "progeny plant," and/or "offspring" refer to a plant generated from a vegetative or sexual reproduction from one or more parent plants. A progeny plant may be obtained by cloning or selfing a single parent plant, or by crossing two parental plants and includes selfings as well as the F1 or F2 or still further generations. An F1 is a first-generation offspring produced from parents at least one of which is used for the first time as donor of a trait, while offspring of second generation (F2) or subsequent generations (F3, F4, and the like) are specimens produced from selfings or crossings of F1s, F2s and the like. Thus, an F1 can be a hybrid resulting from a cross between two true breeding parents (the phrase "true-breeding" refers to an individual that is homozygous for one or more traits), while an F2 can be an offspring resulting from self-pollination of the F1 hybrids.

As used herein, the term "reference sequence" refers to a defined nucleotide sequence used as a basis for nucleotide sequence. The reference sequence for a marker, for example, can be obtained by genotyping a number of lines at the locus or loci of interest, aligning the nucleotide sequences in a sequence alignment program, and then obtaining the consensus sequence of the alignment. Hence, a reference sequence identifies the polymorphisms in alleles at a locus. A reference sequence may not be a copy of an actual nucleic acid sequence from any particular organism; however, it is useful for designing primers and probes for actual polymorphisms in a locus or loci.

Genetic Mapping

Genetic loci correlating with particular phenotypes, such as enhanced sugary trait, can be mapped in an organism's genome. By identifying a marker or cluster of markers that co-segregate with a trait of interest, the breeder is able to rapidly select a desired phenotype by selecting for the proper marker (a process called marker-assisted selection, or MAS). Such markers may also be used by breeders to design genotypes in silico and to practice whole genome selection.

The present invention provides markers associated with enhanced sugary trait. Detection of these markers and/or other linked markers can be used to identify, select and/or produce plants having enhanced sugary trait and/or to eliminate plants from breeding programs or from planting that do not have enhanced sugary trait.

Markers Associated with Enhanced Sugary Trait

Molecular markers are used for the visualization of differences in nucleic acid sequences. This visualization can be due to DNA-DNA hybridization techniques after digestion with a restriction enzyme (e.g., an RFLP) and/or due to techniques using the polymerase chain reaction (e.g., SNP, STS, SSR/microsatellites, AFLP, and the like). In some embodiments, all differences between two parental genotypes segregate in a mapping population based on the cross of these parental genotypes. The segregation of the different markers can be compared and recombination frequencies can be calculated. Methods for mapping markers in plants are disclosed in, for example, Glick & Thompson (1993) *Methods in Plant Molecular Biology and Biotechnology*, CRC Press, Boca Raton, Fla., United States of America; Zietkiewicz et al. (1994) *Genomics* 20:176-183.

The recombination frequencies of genetic markers on different chromosomes and/or in different linkage groups are generally 50%. Between genetic markers located on the same chromosome or in the same linkage group, the recombination frequency generally depends on the physical distance between the markers on a chromosome. A low recombination frequency typically corresponds to a low genetic distance between markers on a chromosome. Comparison of all recombination frequencies among a set of genetic markers results in the most logical order of the genetic markers on the chromosomes or in the linkage groups. This most logical order can be depicted in a linkage map. A group of adjacent or contiguous markers on the linkage map that is associated with a trait of interest can provide the position of a locus associated with that trait.

Thus, the methods provided herein can be used for detecting the presence of one or more enhanced sugary trait markers in corn plant or germplasm, and can therefore be used in methods involving marker-assisted breeding and selection of corn plants having enhanced sugary trait.

In some embodiments, methods for detecting the presence of a marker associated with enhanced sugary trait in a corn plant or germplasm can comprise providing an oligonucleotide or polynucleotide capable of hybridizing under stringent hybridization conditions to a nucleotide sequence of as disclosed herein, contacting the oligonucleotide or polynucleotide with genomic nucleic acid (or a fragment thereof, including, but not limited to a restriction fragment thereof) of the corn plant or germplasm, and determining the presence of the marker by the specific hybridization of the oligonucleotide or polynucleotide to the corn genomic nucleic acid (or the fragment thereof).

The presently disclosed subject matter thus also relates to methods for identifying, selecting, and/or producing corn plants having enhanced sugary trait, comprising detecting in a donor corn plant the presence of a genetic marker associated with enhanced sugary trait (e.g., an se1 deletion as described herein) and transferring the nucleotide sequence comprising the genetic marker thus detected from the donor corn plant to a recipient corn plant. This allows the breeder to develop corn plants having enhanced sugary trait. The transfer of the nucleotide sequence can be performed by any of the methods described herein and/or as are well known in the art.

Thus, methods for identifying, selecting and/or producing a corn plant or germplasm with enhanced sugary trait can comprise detecting the presence of a genetic marker associated with enhanced sugary trait. The marker can be detected in any sample taken from a corn plant or germplasm, including, but not limited to, the whole plant or germplasm, a portion of said plant or germplasm (e.g., a cell, leaf, seed, etc, from said plant or germplasm) or a nucleotide sequence from said plant or germplasm.

Exemplary Assay Primers for Genotyping and/or Amplification

As discussed herein, in some embodiments of this invention, a marker can be identified using amplification products generated by amplifying a corn nucleic acid with two or more oligonucleotide primers. In some embodiments, the amplification is by PCR, and the primers are PCR primers that are designed to hybridize to opposite strands of the corn genomic DNA (e.g., chromosome 2) in order to amplify a corn genomic DNA sequence present between the sequences to which the PCR primers hybridize in the corn genomic DNA. Methods of amplifying nucleic acids are well known in the art.

Accordingly, in some embodiments of the present invention, a method of identifying and/or selecting a corn plant or germplasm having enhanced sugary trait is provided, the method comprising: detecting, in said corn plant or germplasm, the presence of a genetic marker associated with enhanced sugary trait, wherein said marker is detected in amplification products from a nucleic acid sample isolated from said corn plant or germplasm using a probe, said amplification products having been produced, for example, using pairs of amplification primers wherein said amplification primers can have the nucleotide sequences of: SEQ ID NO:1 and/or SEQ ID NO:2 as forward primers and SEQ ID NO:3 as a reverse primer, thereby identifying and/or selecting a corn plant or germplasm having enhanced sugary trait.

In other embodiments, a method of producing a corn plant or germplasm having enhanced sugary trait is provided, the method comprising: (a) detecting, in said corn plant or germplasm, the presence of a genetic marker associated with enhanced sugary trait, wherein said marker is detected in amplification products from a nucleic acid sample isolated from said corn plant or germplasm using a probe, said amplification products having been produced using pairs of amplification primers, wherein, for example, said amplification primers have the nucleotide sequences of: SEQ ID NO:1 and/or SEQ ID NO:2 as forward primers and SEQ ID NO:3 as a reverse primer; and (b) producing a corn plant from said corn germplasm, thereby producing a corn plant or germplasm having enhanced sugary trait.

Marker-Assisted Selection

The subject matter disclosed herein also relates to methods for producing corn plants having enhanced sugary trait comprising detecting the presence of a genetic marker associated with enhanced sugary trait in a donor corn plant according to the methods as described herein and transferring a nucleic acid sequence comprising at least one genetic marker thus detected from the donor corn plant to a recipient corn plant. The transfer of the nucleic acid sequence can be performed by any method known in the art.

Thus, the present invention encompasses methods of plant breeding and methods of selecting/identifying plants, in particular corn plants, particularly cultivated corn plants as breeder plants for use in breeding programs or cultivated corn plants having desired genotypic or potential phenotypic properties, in particular related to producing valuable corn, also referred to herein as commercially valuable plants. Herein, a cultivated plant is defined as a plant being purposely selected or having been derived from a plant having been purposely selected in agricultural or horticultural practice for having desired genotypic or potential phenotypic properties, for example a plant obtained by inbreeding.

The presently disclosed subject matter thus also provides methods for selecting a corn plant having enhanced sugary trait, comprising detecting in the plant the presence of one or more markers associated with enhanced sugary trait as defined herein. In an exemplary embodiment of the presently disclosed methods for selecting such a plant, the method comprises providing a sample of genomic DNA from a corn plant; and (b) detecting in the sample of genomic DNA at least one genetic marker associated with enhanced sugary trait. In some embodiments, the detecting comprises identifying the presence of a se1 deletion that is associated with enhanced sugary trait.

The providing of a sample of genomic DNA from a corn plant can be performed by standard DNA isolation methods well known in the art.

The detecting of a genetic marker (e.g., a deletion in a gene) can in some embodiments comprise the use of one or more primer pairs that can be used to produce one or more amplification products that can be used in the detection of genetic markers. Such primer pairs can comprise, in some embodiments, nucleotide sequences as set forth in SEQ ID NOs:1-3 (e.g., a primer pair comprising, consisting essentially of or consisting of the nucleotide sequence of SEQ ID NO:1 as a forward primer and the nucleotide sequence of SEQ ID NO:3 as a reverse primer; and/or a primer pair comprising, consisting essentially of or consisting of the nucleotide sequence of SEQ ID NO:2 as a forward primer and the nucleotide sequence of SEQ ID NO:3 as a reverse primer).

In some embodiments, the detecting of a genetic marker can comprise the use of a nucleic acid probe having a nucleotide base sequence that is substantially complementary to the nucleic acid sequence defining the genetic marker and which nucleic acid probe specifically hybridizes under stringent conditions with a nucleic acid sequence defining the genetic marker. A suitable nucleic acid probe can for instance be a single strand of the amplification product corresponding to the marker.

The presently disclosed subject matter thus also relates to methods for producing a corn plant having enhanced sugary trait, comprising detecting the presence of a genetic marker associated with enhanced sugary trait in a donor corn plant according to the presently disclosed subject matter as described herein and transferring a nucleotide sequence comprising at least one genetic marker thus detected, or an enhanced sugary trait-conferring part thereof, from the donor plant to a recipient corn plant. The transfer of the nucleic acid sequence can be performed by any of the methods described herein.

An exemplary embodiment of such a method comprises the transfer of the nucleic acid sequence from a donor corn plant into a recipient corn plant by crossing the plants by introgression. This transfer can be accomplished by using traditional breeding techniques. Loci associated with the desired trait are introgressed in some embodiments into commercial corn varieties using marker-assisted selection (MAS) or marker-assisted breeding (MAB). MAS and MAB involve the use of one or more of the molecular markers, identified as having a significant likelihood of co-segregation with a desired trait, and used for the identification and selection of those offspring plants that contain one or more of the genes that encode for the desired trait. MAB can also be used to develop near-isogenic lines (NIL) comprising one or more markers of interest, allowing a more detailed study of an effect of such marker(s). MAB is also an effective method for development of backcross inbred line (BIL) populations. Corn plants developed according to these embodiments can in some embodiments derive a majority of their traits from the recipient plant, and derive the desired trait (e.g., enhanced sugary trait) from the donor plant. MAB/MAS techniques increase the efficiency of backcrossing and introgressing genes using marker-assisted selection (MAS) or marker-assisted breeding (MAB).

Thus, traditional breeding techniques can be used to introgress a nucleic acid sequence associated with enhanced sugary trait into a recipient corn plant. Thus, for example, inbred enhanced sugary trait plant lines can be developed using the techniques of recurrent selection and backcrossing, selfing, and/or dihaploids, or any other technique used to make parental lines. In a method of recurrent selection and backcrossing, enhanced sugary trait can be introgressed into a target recipient plant (the recurrent parent) by crossing the recurrent parent with a first donor plant, which differs from the recurrent parent (i.e., non-recurrent parent). The recurrent parent is a plant that lacks enhanced sugary trait but, in some embodiments, possesses commercially desirable characteristics, such as, but not limited to (additional) disease and/or insect resistance, valuable nutritional characteristics, valuable abiotic stress tolerance (including, but not limited to, drought tolerance, salt tolerance), and the like. In some embodiments, the non-recurrent parent exhibits enhanced sugary trait and comprises a nucleic acid sequence that is associated with enhanced sugary trait. The non-recurrent parent can be any plant variety or inbred line that is cross-fertile with the recurrent parent.

In some embodiments, the progeny resulting from a cross between the recurrent parent and non-recurrent parent are backcrossed to the recurrent parent. The resulting plant population is then screened for the desired characteristics, which screening can occur in a number of different ways. For instance, the population can be screened using phenotypic screens or quantitative bioassays as known in the art. Alternatively, instead of using bioassays, MAB can be performed using one or more of the hereinbefore described molecular markers, hybridization probes, or polynucleotides to identify those progeny that comprise a nucleic acid sequence encoding a marker for enhanced sugary trait. Also, MAB can be used to confirm the results obtained from the quantitative bioassays. In some embodiments, the markers defined herein are suitable to select proper offspring plants by genotypic screening.

Following screening, F1 hybrid plants that exhibit an enhanced sugary phenotype or, in some embodiments, the genotype, and thus comprise the requisite nucleic acid sequence associated with enhanced sugary trait, are then selected and backcrossed to the recurrent parent in order to allow for the corn plant to become increasingly inbred. The process of selecting and backcrossing can be repeated for a number of generations (e.g., for one, two, three, four, five, six, seven, eight, or more generations).

Thus, a marker that demonstrates linkage with a locus affecting a desired phenotypic trait provides a useful tool for selection of the trait in a plant population. This is particularly true where the phenotype is difficult to assay or occurs at a late stage in plant development. Since marker assays are less laborious and take up less physical space than field phenotyping, much larger populations can be assayed, increasing the chances of finding a recombinant plant with the target segment from the donor line that is moved to the recipient line. The closer the linkage, the more useful the marker, as recombination is less likely to occur between the marker and the gene that causes or imparts the trait. In addition, having flanking markers can decrease the chance that false positive selection will occur. Ideally, a marker is in the gene itself, so that recombination cannot occur between the marker and the gene. Such a marker is called a "perfect marker."

Accordingly, the genetic markers of the present invention can be used in marker-assisted selection methods to identify and/or select and/or produce progeny having enhanced sugary trait. Such methods can include crossing a first corn plant or germplasm with a second corn plant or germplasm, wherein the first corn plant or germplasm comprises a marker associated with enhanced sugary trait, and selecting a progeny plant that possesses the marker. Therefore, in one embodiment of the present invention, a method of producing a corn plant having enhanced sugary trait is provided, the method comprising: (a) detecting, in a corn germplasm, the presence of a genetic marker associated with enhanced sugary trait, wherein said marker comprises, consists essentially of, or consists of an approximately 0.6 kb deletion within the region defined by positions 229,915,398 and 230,055,870 as set forth in the bacterial artificial chromosome having Maize Genetic and Genomics Database Accession No. AC217415;

and (b) producing a corn plant from said corn germplasm, thereby producing a corn plant having enhanced sugary trait.

In other embodiments, the present invention provides a method of introgressing an enhanced sugary trait marker into a corn germplasm that is lacking the enhanced sugary trait marker, the method comprising: (a) crossing a donor parental corn line comprising a genetic marker associated with enhanced sugary trait with a recurrent parental corn line that lacks said marker to produce progeny; (b) selecting progeny comprising said marker and backcrossing said progeny with the recurrent parental corn line, wherein said progeny are selected by detecting, in their genomes, the presence of the marker associated enhanced sugary trait, wherein the marker comprises; (c) backcrossing the selected progeny of (b) with the recurrent parental corn line to produce further progeny; and (d) repeating steps (b) to (c) one or more times (e.g., one, two, three, four, five, six, seven, eight, nine, ten, or more times), thereby introgressing the enhanced sugary trait marker into the recurrent parental line, and thus introgressing the enhanced sugary trait marker into the corn germplasm that is lacking the enhanced sugary trait marker.

In some embodiments, a method for introgressing an enhanced sugary trait marker into a corn germplasm lacking the marker can comprise: (a) crossing a corn plant identified, selected or produced according to any of the methods described herein with a second corn plant lacking the enhanced sugary marker to produce a segregating population of plants; (b) screening the plants from the segregating population of (a) for the enhanced sugary trait marker by detecting, in the plants from the segregating population, the presence of a genetic marker associated with enhanced sugary trait as described herein; and (c) selecting a plant from (b) in which the genetic marker is detected, thereby introgressing an enhanced sugary trait marker into the corn germplasm.

In other embodiments of this invention, a method of for producing an inbred corn plant that is homozygous for an enhanced sugary trait marker is provided, the method comprising: (a) selecting a first donor parental line having an enhanced sugary trait marker by detecting, in the first donor parental line, a genetic marker associated with enhanced sugary trait as described herein; (b) crossing the first donor parental line with a second parental line in hybrid combination to produce a segregating plant population; (c) screening the plants from the segregating population of (b) for the enhanced sugary trait marker by detecting, in the plants from the segregating population, the presence of the genetic marker associated with enhanced sugary trait as described herein; (d) selecting plants from the population of (c) having the genetic marker associated with enhanced sugary trait; and (e) screening the selected plants of (d) to identify an inbred corn plant that is homozygous for the enhanced sugary trait marker, thereby producing an inbred corn plant that is homozygous for the enhanced sugary trait marker.

Corn Plants, Parts Thereof, and Germplasms Having Enhanced Sugary Trait Marker

The present invention provides corn plants and germplasms having enhanced sugary trait. As discussed above, the methods of the present invention can be utilized to identify, produce and/or select a corn plant or germplasm having enhanced sugary trait. In addition to the methods described above, a corn plant or germplasm having enhanced sugary trait may be produced by any method whereby a marker associated with enhanced sugary trait is introduced into the corn plant or germplasm by such methods that include, but are not limited to, transformation (including, but not limited to, bacterial-mediated nucleic acid delivery (e.g., via Agrobacteria)), viral-mediated nucleic acid delivery, silicon carbide or nucleic acid whisker-mediated nucleic acid delivery, liposome mediated nucleic acid delivery, microinjection, microparticle bombardment, electroporation, sonication, infiltration, PEG-mediated nucleic acid uptake, as well as any other electrical, chemical, physical (mechanical) and/or biological mechanism that results in the introduction of nucleic acid into the plant cell, or any combination thereof), protoplast transformation or fusion, a double haploid technique, embryo rescue, or by any other nucleic acid transfer system.

"Introducing" in the context of a plant cell, plant and/or plant part means contacting a nucleic acid molecule with the plant, plant part, and/or plant cell in such a manner that the nucleic acid molecule gains access to the interior of the plant cell and/or a cell of the plant and/or plant part. Where more than one nucleic acid molecule is to be introduced these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into plant cells in a single transformation event, in separate transformation events, or, e.g., as part of a breeding protocol. Thus, the term "transformation" as used herein refers to the introduction of a heterologous nucleic acid into a cell.

Thus, a corn plant, or part thereof, having enhanced sugary trait, obtainable by the methods of the presently disclosed subject matter, are aspects of the presently disclosed subject matter. The corn plant or germplasm may be the progeny of a cross between a variety of corn and a second variety of corn that comprises an enhanced sugary trait marker.

The corn plant or germplasm may be the progeny of an introgression wherein the recurrent parent is a variety of corn and the donor comprises an enhanced sugary trait marker.

The corn plant or germplasm may be the progeny of a cross between a first variety of corn (e.g., a tester line) and the progeny of a cross between a second variety of corn (e.g., a recurrent parent) and a variety of corn that comprises an enhanced sugary trait marker (e.g., a donor).

The corn plant or germplasm may be the progeny of a cross between a first variety of corn and the progeny of an introgression wherein the recurrent parent is a second variety of corn and the donor comprises an enhanced sugary trait marker.

Another aspect of the presently disclosed subject matter relates to a method of producing seeds that can be grown into corn plants with enhanced sugary trait. In some embodiments, the method comprises providing a corn plant having an enhanced sugary trait marker, crossing the corn plant with another corn plant, and collecting seeds resulting from the cross, which when planted, produce corn plants with enhanced sugary trait.

Accordingly, the present invention provides improved corn plants, seeds, and/or tissue cultures produced by the methods described herein. In further embodiments, the present invention provides introgressed corn plants and/or germplasm produced by the methods described herein.

The following examples are included to demonstrate various embodiments of the invention and are not intended to be a detailed catalog of all the different ways in which the present invention may be implemented or of all the features that may be added to the present invention. Persons skilled in the art will appreciate that numerous variations and additions to the various embodiments may be made without departing from the present invention. Hence, the following descriptions are intended to illustrate some particular embodiments of the invention, and not to exhaustively specify all permutations, combinations and variations thereof.

EXAMPLES

Example 1

Identification of 615 bp Deletion Associated with Enhancer of Sugary (se1) Trait Two sweet corn isolines, 1756 and 1763, (University of Wisconsin) were obtained to more accurately map the se1 locus in sweet corn. Both isolines had been previously phenotyped for the se1 trait. Isoline 1756 displays the se1 phenotype or trait while isoline 1763 did not display the se1 phenotype. In order to detect the se1 trait by visible phenotype, the recessive mutation sugary1 (su1) must also be present in a homozygous state. These two corn lines, 1756 and 1763, are near isogenic lines meaning that they are nearly identical to each other at all genetic loci excluding the genetic locus that is responsible for the se1 trait or phenotype.

A genomic sequence corresponding to the BAC AC217415 was sequenced in both of the 1756 and 1763 lines. A comparison of the sequences generated from 1756 and 1763 identified a 615 bp deletion (SEQ ID NO:4; also shown herein as the nucleotides at position 10,028 to position 10,642 in the nucleotide sequence of SEQ ID NO:6) present in 1756 and absent in 1763. While not to be limited by theory, the approximately 615 bp deletion appears to be a genomic aberration that can be used as a marker that is tightly associated with the se1 trait. The presence of the deletion is associated with se1 (enhanced sugary trait or phenotype) while the absence of the deletion is associated with a lack of enhanced sugary trait or phenotype. BAC AC217415 has been mapped in the maize genome to chromosome 2 and a region that has been previously associated with the se1 trait.

Example 2

PCR Assay (SM2293AQ) for Detection of se1 Trait

The PCR reaction designated SM2293AQ was designed to detect the 615 bp deletion described in Example 1. The SM2293AQ PCR assay was performed using a 96 well plate (Axygen Scientific #PCT-96-FS-C). Approximately 20 ng of genomic DNA (see Example 3) was added to the wells of the plate and dried in an oven at 140 degrees F. for approx 3 hours such that no liquid remained in the well. To each well was added the following components for the PCR reaction: 10 uL of 2× Sigma JumpStart Taq ReadyMix (cat #P2693) with 5 mM MgCl2, 0.5 ul of primer mix (36 uM of each primer) (SEQ ID NOs:1, 2 and 3) and 9.5 uL of water. The plate was then covered in a sealing film (VWR #82018-844) and loaded into a thermocycler (Applied Biosystems GeneAmp PCR System 9700). The thermocycler conditions were 2 min 50 degrees C., 10 mins 95 degrees C. and 40 times cycle through the following: 15 seconds 95 degrees C., 1 minute 60 degrees C., and ending with 5 mins at 72 degrees and hold at 25 degrees C. The contents of each well were then analyzed on an agarose gel.

A 3% agarose gel was prepared by combining 275 mL of 10×TBE (Amresco #0658-4L), 8.25 gm SFR Agarose (Amresco #J234-250G) and 7.5 microL of ethidium bromide solution (Fisher #802511). This solution was boiled until the agarose melted and then was allowed to cool to approximately 65 degrees C. before being poured into the gel tray containing a comb. The agarose solution was allowed to solidify in the gel tray at room temperature.

The PCR reaction was combined with 10× loading dye (150 mL glycerol (VWR #JT4043-00), 350 mL deionized water, 0.01 gm xylene cyanol FF (BioRad #161-0423), 0.01 gm bromophenol blue (BioRad #161-040) such that the loading dye represents 10% of the final volume to be loaded into the gel.

The agarose gel was loaded into the electrophoresis unit and covered with running buffer (0.5×TBE) prior to loading the wells with the PCR reaction and loading dye mixture. Electrophoresis of the PCR samples was performed at 110 volts for approximately 2 to 3 hours. The gel was then visualized by exposing the gel to ultraviolet light, which causes the size separated, ethidium bromide stained DNA bands from the PCR reaction to fluoresce. An image of the fluorescing gel was captured using a Kodak Electrophoresis Documentation and Analysis System 290 (EDAS).

Two PCR products (also called amplicons) were observed when the SM2293AQ PCR reaction was run on an agarose gel. The sizes of these amplicons were approximately 110 bp and 170 bp. The 170 bp amplicon was expected if a 615 bp deletion was present in this region of the genome. No amplicon was expected if the 615 bp deletion was not present. As expected, the SM2293AQ PCR assay when performed on a variety of inbred sweet corn lines, showed either the presence, or absence of the 170 bp amplicon; however there was also an unexpected 110 bp amplicon generated. While not to be limited by theory, it is suspected that this unexpected 110 bp amplicon was generated by the primers binding to unlinked chromosomal regions in the genome.

It is envisioned that other primers can be used to detect the 615 bp deletion. For example, a primer pair comprising, consisting essentially of or consisting of the nucleotide sequence of SEQ ID NO:1 as a forward primer and the nucleotide sequence of SEQ ID NO:3 as reverse primer can be used in a PCR reaction to detect the 615 bp deletion. Other suitable candidates for primer sequences can be obtained by analysis of the genomic DNA 5' and 3' of the 615 bp deletion. One of skill in the art would be able to determine the appropriate PCR conditions for a suitable primer pair of this invention.

Example 3

Genomic DNA Isolation

Genomic DNA is isolated from plant leaves by collecting 3 leaf tissue discs approximately the size of a paper whole punch and placing the leaf discs into an Eppendorf Tube® which contains 3 metal beads. The plant tissue is frozen by placing the tubes on dry ice and then the tissue is pulverized by shaking the Eppendorf Tube® so the metal beads pulverize the frozen plant tissue into a powder. The pulverized plant tissue is resuspended in 0.8 mL of pre-warmed (60° C.) CTAB extraction buffer (2% CTAB (hexadecyltrimethylammonium bromide), 100 mM Tris HCl [pH=8], 20 mM EDTA, 1.4M NaCl) and mixed well. The contents of the Eppendorf Tube® are combined with 0.2% β-mercaptoethanol, 0.1 mg/mL proteinase K and incubated at 60° C. for 1 hour. This mixture is extracted by combining with 0.8 mL of chloroform/isoamylalcohol (24:1) solution and gently mixing for 2 min by inverting the tube. The phases of this solution are separated by spinning the tube for 10 min at 14000×g at 4° C. The aqueous phase (above the white interface layer) is transferred to a clean Eppendorf Tube®.

RNA is removed from the aqueous phase by combining with 1 μL RNase (DNase-free) and incubating for 30 min at 37° C. The mixture is extracted by combining with about 0.6 mL of isopropanol and mixing by gently inverting the tube and incubating for 2 hr to overnight at room temperature to allow for precipitation of the DNA. The DNA is recovered by spinning the tube for 15 mins at 14000×g at 4° C., which causes the DNA to pellet into the bottom of the tube. The supernatant is removed and the pellet is washed once or twice with −20° C. 70% EtOH and spun for 15 mins at 14000×g at 4° C. The supernatant is removed and the pellet is allowed to dry by leaving the tube open at room temperature. The pellet is resuspended in sterile H₂O or TE (pH 8.0) and can be stored at −20° C.

Example 4

Validation of TaqMan® Assay in Wide Range of Sweet Corn Inbreds

A wide variety of inbred corn lines were selected to determine if the 615 bp deletion correlated with the presence of the se1 trait in diverse genetic backgrounds of sweet corn. A large collection of sweet corn inbred lines were obtained which represent a wide genetic diversity in sweet corn. The lines were previously characterized for the presence of starch mutants such as sugary (su1), shrunken 2 (sh2) and enhancer of sugary (se1). Each of these starch mutant traits are recessive traits which must be present in a homozygous state in order to be observed phenotypically. Individuals from a variety of lines were sprouted and green tissue was collected for isolation of DNA for PCR analysis. DNA isolation and analysis of the 615 bp deletion by PCR was performed essentially as described in Example 2. The data generated on the sweet corn inbreds are outlined in Table 1.

These data demonstrate that the TaqMan® assay of Example 2 is able to detect the 615 bp deletion in a wide range of sweet corn genetics. In addition, the 615 bp deletion is tightly associated with the presence of the se1 trait. Most of the inbred lines which display the se1 trait also produce a PCR product of 170 bp in the TaqMan® assay of Example 2. These data indicate that the 615 bp deletion can be used as a marker for the se1 trait in further breeding of sweet corn lines. The assay of Example 2 is one method that can be used to track the presence of the deletion; however, other molecular assays (PCR based or DNA based) can be used to detect the presence of the deletion, as are well known in the art.

Example 5

Linkage of 615 bp Deletion and se1 Trait

The 615 bp deletion was further confirmed to be tightly associated with the se1 trait by correlation of the presence of the deletion and presence of the se1 trait in a segregating F2 population. The reverse correlation was also analyzed, which is the absence of the deletion and the absence of se1 trait. A recombination event is defined as either the presence of the deletion and absence of the se1 trait; or as the absence of the deletion and the presence of the se1 trait. A recombination event can be used to determine the genetic distance between the marker (i.e., detection of the 615 bp deletion) and gene or gene locus which is responsible for the se1 trait. Determining genetic distance is a standard technique used by one of ordinary skill in the art.

The segregating F2 population was generated by crossing the two isolines 1756 and 1763, which are described in Example 1. F2 progeny were developed by crossing these 2 lines to first generate an F1 population as seed. The F1 population was planted and the resulting plants were allowed to self fertilize to generate the F2 population which was used for fine mapping purposes. Individuals from the F2 population were evaluated for the presence/absence of the se1 trait and for the presence/absence of the 615 bp deletion. The se1 trait was identified by the phenotypic characterization of the presence of a lighter yellow kernel color, slower rate of kernel moisture loss when drying, and a finely wrinkled pericarp in mature dry kernels. Detection of the deletion was performed by a PCR based assay essentially as described in Example 2. 1817 individuals from the F2 population were evaluated for both the genotype (deletion) and phenotype (se1 trait).

Strong correlation between the presence of the deletion (as detected by the PCR assay performed essentially as described in Example 2) and the presence of the se1 phenotype was observed. The reverse correlation of absence of the deletion and absence of the se1 phenotype was also observed. Only one plant of the 1817 individuals was identified as a recombinant where the plant showed the presence of the deletion and the absence of the se1 trait. Using standard genetic mapping techniques, this analysis indicates that the 615 bp deletion is 0.07 centiMorgans away from the genetic locus that is responsible for the se1 trait. The data describe a correlation between the presence of the deletion and enhanced sugary trait (se1). This correlation was not 100% as there was one individual that showed the se1 trait but did not have the deletion.

The above examples clearly illustrate the advantages of the invention. Although the present invention has been described with reference to specific details of certain embodiments thereof, it is not intended that such details should be regarded as limitations upon the scope of the invention except as and to the extent that they are included in the accompanying claims.

Throughout this application, various patents, patent publications and non-patent publications are referenced. The disclosures of these patents, patent publications and non-patent publications in their entireties are incorporated by reference herein into this application in order to more fully describe the state of the art to which this invention pertains.

TABLE 1

Variety of sweet corn inbred lines evaluated for presence/absence of the 615 bp deletion and association of presence/absence of the deletion with the enhanced sugary phenotype.

| Plant name | Starch mutant trait based on phenotypic evaluation (+ = se1 phenotype; − = Se1 phenotype(non-mutant)) | PCR products detected |
|---|---|---|
| SWC001 | − | 110 |
| SWC002 | − | 110 |
| SWC003 | + | 170 |
| SWC004*** | −*** | 110 and 170*** |
| SWC005 | + | 170 |
| SWC006 | + | 170 |
| SWC007 | + | 170 |
| SWC008 | − | 110 |
| SWC009 | + | 170 |
| SWC010 | + | 110 and 170 |
| SWC011 | + | 170 |
| SWC012 | + | 110 and 170 |
| SWC013 | + | 170 |
| SWC014 | − | 110 |
| SWC015 | + | 170 |
| SWC016 | − | 110 |
| SWC017 | + | 110 and 170 |
| SWC018 | + | 170 |
| SWC019 | + | 170 |
| SWC020 | − | 110 |
| SWC021 | − | 110 |

***This inbred line indicates that the correlation between presence of the 615 bp deletion and presence of the enhanced sugary trait is not 100%.

Sequences:
SEQ ID NO:1 GCACGTCAGACGGAGAGATAG (forward primer 1 for TaqMan® and agarose gel assay)
SEQ ID NO:2 CGCCCGATCGAGTGACAAC (forward primer 2 for Taqman® assay)
SEQ ID NO:3 ATGGCTCTCGCTGACGAACAC (reverse primer for Taqman® assay)
SEQ ID NO:4 (the deleted sequence associated with the trait)

GTGCACACCGTGGAGTGGACGGCGGAGGAGCGCTCTCTCGATGATCCGGCC

AGCGCCGTGGGTGGGCGCCGGGCACCGCGGGCGGGGCGGCGAGGCGGGCGC

CTGCACCGAGAGCCTCGGCTCCGAGAGTGGCGACGTCGGCTGCGACGCCGC

CGAGATCGACCAGTTCTTCCCGCCGGCGCCGGCTGCTGGCGGCCCGGACGA

CGCCGGCGCAGAGCCCTGCATTCCGGACCTGGCGGCGGCGGCGGCGGCAGG

GAAAAGGCGGCGCGGGGGCTTCCCCCCGCCGATGCCGCGCGCGTCGGGGCC

GCTGTTCCTGCGCGCGGAGCGCCGCGGCGGCCGCCTCATCCTCACCGAGGT

GCGCGCCGACGAGCGTGAGCGCCGCGTTGTGTTCCGCGCCGAGCGCGACGG

CGGACGCCTCCGCCTGCGCTTCGCCAACGACGGCGACGGCCCCGAGGCGGC

AGGTGGTGGTGGCGGCGCCGGCGGTGGAGGCGGGGAGCTTTGTCAGGTGGC

CGCCGGCCGGAGGGGCGTGCAGGTCGGCGCGGTCATGATGGGGGCTATCTG

AAGGAGGGCCGCCCGATCGAGTGACAACGAGACGCCGGCCGGCAGCAGATT

GCT

SEQ ID NO:5 (the manufactured junction fragment in the lines with the deletion)

GGCCGGCAGTGGCCTAGCTTGTTCCATTCATCCACTCAGCCGGTCGTTGCC

GATGGTCGAGAGAGAGAGAG

SEQ ID NO:6 This sequence resides on Chromosome 2, Bin 2.09. In the most recent build of the maize physical map (Maize_B73_RefGen_v2), this sequence resides at positions 229972938-229986386. The 615 basepair deletion as set forth in SEQ ID NO:4 is located at nucleotides 10,028-10,642 of SEQ ID NO:6.
>AC217415_2 [Bold 14 pt type=615 bp InDel; Bold 16 pt type=forward primers (2) of agarose marker; Bold 18 pt type=reverse primer of agarose marker]

AATACTAAAAAAACACAGAAAGTATACTCAATAGTTGGCATCAGAAAATAAATAAA
GATGACAATAAGAATACCACAATCTACCCTGACTGATCTACCTGGCCAGAGCAGAA
CGGCCCAACTCAGATGCCTTTTTTGTAATCTTCATGTGCTCCTAAAAGAGTCCATATA
TATTCTAGAAGTAATTTTTTTTGAAATAAAAGTTACTGTAGGGGGGCTACAGTATTT
TATTGCTTAAGGAAAAAAGGGGTATAGATACAGAAGGGTAAGTACAGAAAGGAA
AATGAAAGTTACAGCACAGAAAGCTGAAGCCAGGTTTTAATTTTATCTCCTATTACT
GGCTTAACTCGATGACATAGAAGGTTCATTTCTGATTTGAACATATCTCGACAACCT
TCCACCGTGGGCGGAATCTCAATGAACACCCAATTATTTCTGCATTTTCAGATGCCC
CAGGTCAATAAGATTATAGCTTCAAGTTTCCAGGGGACTTGCCAACGTCTTCTGATT
CTCAAAATGGTTGTGAATAAGTCAGCAGAACGTGATGGAGAGATTCCTACCAAGGA
CCAACATCTCCTAGCAAAATTGCATCTGAAAAAAGATGAGTGGCCGTCTCTTCAAC
TTGGAGAATACAATTGTCACAGGAGTATGAATCCAGTAACATAGCTCGCTGCCTTAG
AAAAGCTCTGGTATTAAATCTGTCCTTAAGTAGCAGCCAAAAAAACACCTTGTGCTT
GGGTTGACATTTGGATTTCCATAGCCAAGTGAAGATGAGATGTGTCCACTGGTTGCC
CATCAAATGAGAATAAATCTTTTGCGAGGAAAATAAGCTAGAAGAAGTAGAGCAGC
TCCATTTGTCTCTCTGATTATTATGTGGGAGATTATCCAAGCAATCATTCAACTCTTG
AAGTATAAAAAGGCTTCAACGGACAACGGTGCATGGAACATTTCTTGGGCATCAA
CCAATCGTGCTTGTAGGACGGTGATGTCTTTGCATGCAGCGAAGGACCAAAGTTCTG
GATACTGTGTTGATTTGGAAATACCATCCCAGTTATCATGCCAAAGGAGTGTTGATC
TTCCATCTCCAATTTCCACCCTAGCAATTCTCTTAAATGGTTCAAGCGTTTTAAGGAC
ATCTCGCCACCAAAAAACCAACTGGTTTATCCGAGGGCAGAGAGTGACTGTAATGA
TTGGTCCATACAATATTGACCCATGGGATGTCAGCTCTATTGAAGAATTTATGAAGA
TTTTTCATGAGTAGGGCTCTATTTTGTAAAGCCAAATTAATTACACCCAATCCCCCCT
AAAATTTTGGCTTGCAAACCGAATTCCAAGCAACTAGAGGGGGTTTCTTAGCATTTA
AATCAACACCTCTCCAAAGGCAATGCCTTCTGAGTCTGTCATTATGCTTGATCACCG
TTTTGGGGAGCTTAAGGGTGCACATGTAGTATGTTGGAAGAGAGGAGAAGGCTGCA
TTAACCATTTGGAGCCTTCCAGCCTGTGATAAGAAGATGGAGGTTGACGCCAGTCTT
TTTTCAATTTTCTGGATAAGGGGGAGAAAAGCACCCAAGTTGGGTCTCTGAAGACCC

```
AAGGGAAGCCCTAAGTAAGTAAAGGCATTGATCCAATTTTGCAATGAAATGTATTTG
CAAGGATCTCCATTTTCTGGTCCGTGACATTGATGGGATAAATGCTGGATTTATGGT
AATTCACATGAAGCCCAGTGGAGTCAGCAAAAGAATTGAGCATTGCTTTTAAGAAG
AAAAGTTGTCTAGGGCAGACTTCCATTATGAGAATAGTATCGTCGGCATATTGGATG
ATAGGGAAATCCGGACCACAATTGTTTGGTAAGGGAAGACGAAGAATGCCACCTTC
ACAAGCTTTGTTGACAATAGACTGCAGAAGATCAGCTGCAAGAACAAAAGAAGCG
GTGACAAGGATCACCTTGTCTAACACCGTGTCTGCAGTGAAATCTTTTCCTAGGGA
CTCCATTCAAAAGAACTTGTGAAGAACCGGAGCCAAGAATCATAAAAACCCAGTGG
ATCCACTTATCACCGAACCCCTTGTGCCTCAAGATCTCCATAAGAGCTGCATGCTCC
AATTTATCAAATGTCTTTTCAAAATCAAGCTTAAAATGACCATTTCCTTTCTGGATT
TGTGGCAAAGGGAAATATATTCAAAAGCCCATGCTAAGCAATCCTGGATCGATCTAT
CCTTGATGAAACCATATTGATTCTGATGAACTAGCTTTGTGATCACTGGTTGTAAAT
GATTGGCTAAGATTTTTGTTAGTACTTTGACACTCGTGTTAAGGAGGGAGATGGGTC
TATAATCACCAACTGAATCCGGAGAGCTATTTTGGGAATGAGAGTCACATATGACC
CATTAATGCTATGCATGCAGAGAGATCCTTCAAAAAATTGTTGAAAGATCATAG
AAATCAGGGGCAATCACCGGCCAGCATCTTTTAACAAAGTCTGTATTAAAGCCATCT
GGACCTGGCGATTTATTTGATGGCAGACAAGCAATGATTTGATCAATCTCAAGACAA
GAGAAAGGGTGTTCAAGCTCTGACAAATTATCAATCGGCTGAATCAAAGCAGATAA
GTTGAAAACCATGGAATTTTGTTTCATCTTGCTTCTGCTTATAAACAATGAAAAGC
AATTTGGTACAGGCGCTAAACGGAAAGGATTTCGGAAGATAAGCATTGCTTTGTATG
TAGAACTTTCATTTTGACACTTTTTTTTTACCGAGGTAGTTTACAAAATTTAAATTTTG
AATTTGATATACTTAGATTCAATTTTTGAGAACCGAAATGAGTTCAAATAAAAAAAT
TGTCAACTACAAAGTTCCATAACTTTTAGAGATCTATAACTTTTATTTTAGTGGTTTT
GTCATAGGAGGTCGTTTGAAAAACTCGAAAAATTAAGGATAAAAATGATTTTAGTG
GCATGTCCTTAAGAAACCAGGTTTTTTTAAGGAACCGACTGTAGATCTCTAGTGGCG
GTTTTCTTAAGGAATCGGCACTAAAAATAACACAGACGGTTGGTAACCGAATCCATC
TGTACAAATATATCGCTCCGCAGGCTTTGAGCCTTTTCTACTAGTGTGCCCTACCAT
GAATGAAATCAAATTTTCAGGAAAAAATACAATACATTACTTACTCCATGGAAGT
AGGCTGGTTCTCATGGCCTATTTTGAGCTTCTCCTTTTGGGTGGGCCTAATTGGTGG
AAACATTTTATGGGCTAGGCTAACAGCACGCTCTGAATAACACAGGTGGATTCTTCG
TTGAGGGATGCATCTTCATTCTCGTCCACGCGGAGAGAAAAAATCTTTATATGTTTG
```

TCTCCACTAACATTTATGAGAAAGCATTTTCCTCGCATCATTAAACATGCCGGGCAA
TCAATATTTAGAGACAAATGTAAATTAACTACTAGTCGGTTGCTCGTACATTGCAAC
GGCTTACAACAATACACATGTAAACTATCCACAAAAAATCAAGATTTTTTATTGATT
GTCTCCGCTCTCCGTATAATATTTTTTCGATTTGGCTAACTAATGTTATTGTTTACTCC
ATCCAATATGTATTGGTACAACACGATCAATGAAGTGAGCGATTAGAAGAGAGTTC
ACAACGACTGACTGAACGAATAGAAATTATAAAATGGTATAATTCCACCATACAGA
GACCAAATAAGACAAAGTTTGTGAGCTCAAGTTTCTAAAATAAGTCATATGAACTCA
AACTTATAAAAAGATAGATCAAAATATGGAGTGATTGCTAAAATAAGACATCAAT
AAAATCTGGATGTGCTCGATATAAATTATGCTACTTCGTAGCAATTACTAACGTTTA
AAATCAACAAATAACCTTTCATTTACTGTTAGTGTGACAAATCATTGTTGCTCCATC
CAATGCAGCAACCTCAAACACCATTTAGTCTACTGCGTCAATGTGGTCTTAGAAACG
ACCTAATGCTTGCAAGAGCCAAGAAAGTCGTGTCATGCTTGGGTTGTAGCCTCGGCT
CGCAGTGTTGATCCGTCCCAACATGATTATATATATTTTTACGAAAAACGTATAT
ACATATATAAAATTTATATTCAATATTAAAAACATTTGAGTACGATGTTCTACTGATT
AGACAGCTTCACCCAGTGTCTCTCGCCCTTCTTCCATCAGGACATGGTTTCGAACCC
CACCTCCTGCACTGATTTAATCAAATGGGCCGACGGGCTGGCCCGACACAATTAACA
GACCGGCATGACGTACCTGGGCCAGAGTTGTGGCCCACGAGCGTCTGGCCCGTGTT
GGGCCACCGTTTAGCCATCTATAGATGTGGAGCGGGTTAATTTGAAATAACTGAGAG
GTTATTTGTAAAAAATGATGTGGGACGACCGTTGAAACTGGTGCTTTAAGTATAGT
ATAGATATCAAACAAATAAAACTTAAAATTACAAGATATAGCTACTTTAAGCTTTAC
TTTGCTATTTATATTAGGCTAGTATTGAGGTTTTTAGTAGAGTTTTAGCATGTCAAGG
AACTATAATTTAGATCAACGGAAGTTCGTGAGACTGAGTATGTGTGGAACCAGGGG
ACATGAATAGTTCTCTATCCCTGTCTCCAAGAACTCGTCACGGACTAACTTTCCTTGT
TTTGATCCTGTGGGGATTAAATTACCTCCATCCTCATTCCCTAATAGCTAGAAGAATT
TCTCGCGTGAAATCAGAAATCGGGTCCATTATTGTTACCCAAAGTAGACATTGGGGA
TAAACATTTATCAGCAGCCCAGGTTATGCATGCCTGGTTCCGGAGGATAGACATGCA
TGAGTGGAGTGGCCGTTTCCATCTATCTATCGGAACGGAAACGATACATTGGGATGT
GGTCGCGAGATAAGAGAATGGGAGATCTCCAGCAGCCAGCACTGCAGCATGGTATA
GGGTCGTCGGCCGGAGAACCAGCCAACCACGGCCAATGCAAAGCTAGCTGTCACTT
TGGCAACTTGCCGCCAAAATGCAAACCGATACCATGCATGTCCATATATGATATACT
CCTGTGGCTGGTTAGTCACAATGGTAGGCATCCATGGCCTTGAGTTTTCCGAGAACT

AGAGCCAAACTCAAACTTAATCAGGACCATTGGTAACATATAAGCGTCCATCTCCTT
TTTGATAAAGGAAGCTTTATTAATCTTAAACAGTTACATCAAGATGATACAATAGAA
CTAAGATTACTCCTAGTCTCTACACACTAAGTGTACATAGCCAAACAAAAGAGAGG
AAAGAAAAAAAGAAAAGAAACAAAAAGAGAAACAAACTTGTCCTAAAGCGAGCT
ATCACACACAACAGTCTTCACGGCAACCAATAACCAGACAAAGCTAGATTCAAGAT
TGAGGCACTCCATAAGCAACGTCTTCAGGAAGAACACGGCATATAAGAGCGTCGCC
ATTGCGATGACCCAACCAACAAAGGCCAGATCAAAGGTTTTCACCTAAGAGAAAAT
GACCCTCGGTACTTCAGACAATGCCTTCATCAAGGTCGATGCCCGGCATAACCAACT
AAGATTAGGCCTAGAGATTTCACTCCAAAGTCGACGAGCCCAACACCCATATGTTCC
ACCAAATCAAAGAACATCAGTCTTGTCTCCACCTTCTTTCCATGCTCATGCTGACATA
CCACCAAATCTTGGCTAATATCAAACGGCCATAAACTCTGAAACAACATCTAATTTT
AGATAGACATTCCTATGAAGACAGAGTCGCAAACTAGCCAATAGGCACACGAACAC
AGTCCGTAGCTTGCATCTAAAAATAGAATGTGTCGCTCGAGCAAAAATGACCGTCAC
AAAATTATTATGTAATATAAGCCAGAGTCGGACAGAACGACCACTGAATAGAGCTA
AGTGTTGTCTCCAAAGTTGTCCAGGCCGCCTCTCCAAAGTCAATCACTTTATATAGA
CGTTTTTTAGAACCACCAGATGTAGGGATCAGTAAAAATATTTCTTTTTATAGGCG
GTTAATTAAGAAGCGTCAGTGAAAATTGATTTGCACTGGCGGCTCAGTTAAAACAAT
CACCGGTACAAATCGATTTTCACTAGCGGTAGACTTAAGAAAACCACATGTGCAAAT
CTTTTCTAGTATAAATTGGGTTTTAAAAACAGCAAAAAGTGGGTTTTTAAAAACAGC
AAAAATATTTTTATTTGGAGAGGCTCCACTCGCCCGTCTTCGTCAAAGCCGAATTCG
TGTGCTACGCAGCTCCGTAAAAGCCATAAGCCATGGTATTTTTCGCGCAAAATTCAT
GCACTACGCAGCCCATGGCTCTCGAATCCGCAACAACCTCACCGTTGTGCATAACCT
CGTCTACAACTCCACACATCGCTTACTTGTCTCTAAATTACAGTTTTGTTGTGCACAT
ATTAGAACATACCGAGTATAAATTGATTGTTTCAGGTTGTAAACAAATTCAGAAGGT
TATCAACTACAAAATTTAATAATTTTTTAAGTTCTACAACTTATTTGGTACTTTTTCA
TTCGAGGTTGTTTGTAAAATTTGTATTTTAAAATTTATCCAATTTAGATGCAATTTTG
ATAGCCCAAATGACTTTAAATGAAAAGTTATCAACTACAAAGTTTCGTAACTTTTA
GAAATCTATAAATTTTATTTTGGTGGTGTTTTCATACGTGGTCATTTGAAAAAAACTC
AAAAACTTGATTTCAAATGATTTCTACATGCGGTTCCTTAAAAACTGTCACTAGAAA
TACACGATTTATATTGGCAATTTTCTTAAGGAACTGTCAGTACAAATATGATTTCTAC
TGGCGGTTTTATTAAGAAACCCGCCTATAGAAAATGCACGATTTCTACTAGTGTTTT

```
CTTAAGAAAACCACCAGTGAATAAGTGTTTTCACTAACAGTTCTTGAGTCGACACAA
CCAATTTATTTACACTGGCGCTCGATAATCAAAATCGCTTGTAAAAATTATACCTCA
GCGCATGCATAGAGATTTGTTTGTACTATAGTGATAATAATCGTTCCCCGTATGTGA
AACCAAAGTCGGTTAGGCTGACTTCTGGCATATTCTAAAGTGCTTCGTTTATAAATC
GACTTTTGATGTGGCAACCCTAGAGATCATATTTTGGAGTTGTTTTCTAATAGGATA
AGTTCAACCCTATTAATGCCCAAAGAAGGTCATACCTTCACTACCACCAAGATCTCG
ATTTAAGGAAGTTTCTATGGGGGCCAGCTACTGGGGCCACTGCTCCTGGGGCACCAT
GTTCAAGGGGCTTATCCTGGCTTTGGGAAAGATTAGGGCTTGACACTTTGGGCAACA
TGATCTCAGATCATTTTGACTGAATGTCATATATACCACCAAGTCCTCTTAAGAACC
ATTTGGAATGTCTCTTACTAGAACAATTTAAGTCATGGGACACTCATGCCCTAGGGC
ACTAATGAAAGATTCAGATGGCAAAGGCATACCATCCCCTCGAGGAACTTAATGAA
ATACACTTAACCGCTTGAGGCCCTCTACTGGGCCTCAAGTACCTAAGGTCCTTGACC
TCACGTAAAATGAATGGTGGGGCCTTGATCCCCTGAGGCCCAAGGCCTCTTGTGGGA
ACAAGGTACTTGTTATGGCTAGGTGTAATCTTCTCCACAAGACAGGGATGTTTCCTG
TTCCACCGAGCGCACTAATGCCCCAAAGCAAGGACCCTATGTTAGGGCCTACTAAC
AGGTCCATAACACCGACATATCAAATAAGTCTCTTGTGCAACATTATGTGATGTATG
GCATTATAGCCTGATAGGCGCATTATCGCCATGATTTAGGTAGTTGGGTACTTGAGA
CCACTTTTGGTATGTGCATTGATCTTGTAGCCACACATGCACATTTCAATGTACCATA
AAGTATTATCAAGTACAAAATTCTACACCGGCAAAACAAATATGTCGTACCCAACG
ACATTGTTCCTAATGTTCATAGAAGAGATATAACATACTTGGCCTGCAACAATTAAT
TATGGCAGCCATTAAAGAAGGACATCTCTAACACTAGGCTACGACGGAAGGCATTT
GTTGGGGACTTGTTCTCAAATGCTATGAGTTAAGAACAAGGCAACATAGAAAATGTT
AATCGTTAAAGCCCTTCGTCCTTCGAAGCATTATTTCCTTTAGGATATAATGGTTCCT
GGACGAAGGTTATAAATGACGTATTTCCATAAATTCATCATACAGTGACGAAGGAT
GAAATGTAAGGAATATAAAAGACAGCATAAACAATTATTTATTATTATTAGGTATAA
ACAGGAATATCATTGAATTACAAGTGTACCTTCAACTGGAAGGAGATGATATTACA
AGCGTGACGTAAAAAGCGAATGCCAAGTCAGCGTGAACAGTACGGGAGTACTGTTC
ACCTATTTATAGGCGCGGGACACAACCCATACAAAATTACATTCATGCCCTTTACAG
TTGATAATAATTCTATAGTAATCTGTCGAGGTCTAAATAGCCTTTTCATCTTTAAGTC
GGTTTCACTTTCTGCTGTCACGCCGAAGCTTCCTGCTCACACCTTCGGCGCTGTATC
AACCTTCGTATTATTCTGGTCTACTGTGGTGCCGACTTGAGTCCGAAGATACCTGTTC
```

ACACATTATACTCCAGAAATACTGTTAAATCCTGTTTTTGAGGACCTTCGGATGCCG
AAGGTCCCCAACAGCATTGCTTTGAAATATGACTTCACAAACAAGATAATATTGAAG
TGGTTGGGTCTTAGTTGGTGAGATCCAAGATCCAACTGATGTAGCCTCTCTCCTCCCT
TGGTCTATAAAGAGGAGAGCACAGTAATGTTCGAGAGATTTGATTTGGAATTCCAT
AAGCTTTCACTCATAAGGGATTTTTTATTCTTGGTTAGAGACTCTCGTTCACAATATC
TAAGGTTAGGCATAAAGGTGAATTAGGACTAATATGCTAGAACTCCTATCATAATTG
ATTGGAAAGGAGGAGGTAGGATGTCATGGCACTCAATTAAATCTTGAGCTCGCAAT
CTTCTTTACTTTTGTGTTCACCTATCGATAAGTAACAATAGGACATAAGATATTATAT
GCACGCTATGGCCTGAACCTCTTTAAAATTGTCAGTGTGCTAGTTCCCTATTAGGGG
ATGACAATTGGTATGAAACTTGTGGTACACGGGTTAGAAACCGGTACTCACTAAACC
CGCACTCACATCTATTACCCCGTGACGAGTACAATATATTTAGGCACTCGCACGTCG
CACCCGCTACTCTCATATACACCGAGGGCAAATAATTAGACATATTTGACACACACA
TAGACAACATGTCTAGTGTAAAAAGATTAAATTGCTAACATGTTGACATCAAATTT
TGTCCACCAGATTCATCATCTACAGATGAGTACAATTTCACTTGTTCTGACACTGTTT
TAAACCAGCTTGGGTTATTCGTGCTGGGCTGGGCACGAGCTACTACTCCAATGCACG
CGTTGTGCAGCTGGGCTATGGGTGCCACTTGTGCACAAGCTGCCAGCGGCTTTTCGC
CGCGGCCAGCCCAGCCTTGAATTCCTGGAGAGCCTGCCTGGAGGCCCGTGCCCGGCT
CCCTCCCGCTCGCTCTCCCCAGTTGCGCTCCAGCTCAGCAGCTCAGGCGTGCGCCGC
CGCCAGCGCCGCCTCTCCCATACCGGGCAGCGCGGGCCCCACCCGCTCGCTGCCCCG
CACGCCAGTGACCCCGGACCCGATAGGCGTGGGTGCGTGGCGTCCTCGTCCGCCGTC
GCCTACAGCTTAGCTTCTCCCTCCCGCCAGCTCGGAGGCGCCACGCGCCGGGCTCCG
TCCGAAACGGCCGGCTCGCCGGTTCGGAAACTGACGGCGGGGTGGTACACGTCAGC
CCAGGGCCCCGCACGTCAGACGGAGAGATAGGCATCGGCGGGGTAT
ATAAAAGCGCCTCCTCTCGTCCTCCTCGGGCCGGCAGTGGCCTAGCTTGTTCCATTC
ATCCACTCAGCC**GGTGCACACCGTGGAGTGGACGGCGGAGGAGCGCT
CTCTCGATGATCCGGCCAGCGCCGTGGGTGGGCGCCGGGCACCGC
GGGCGGGGCGGCGAGGCGGGCGCCTGCACCGAGAGCCTCGGCTC
CGAGAGTGGCGACGTCGGCTGCGACGCCGCCGAGATCGACCAGTT
CTTCCCGCCGGCGCCGGCTGCTGGCGGCCCGGACGACGCCGGCGC
AGAGCCCTGCATTCCGGACCTGGCGGCGGCGGCGGCAGGGAA**

AAGGCGGCGCGGGGGCTTCCCCCCGCCGATGCCGCGCGCGTCGGG
GCCGCTGTTCCTGCGCGCGGAGCGCCGCGGCGGCCGCCTCATCCT
CACCGAGGTGCGCGCCGACGAGCGTGAGCGCCGCGTTGTGTTCCG
CGCCGAGCGCGACGGCGGACGCCTCCGCCTGCGCTTCGCCAACGA
CGGCGACGGCCCCGAGGCGGCAGGTGGTGGTGGCGGCGCCGGCG
GTGGAGGCGGGGAGCTTTGTCAGGTGGCCGCCGGCCGGAGGGGC
GTGCAGGTCGGCGCGGTCATGATGGGGGCTATCTGAAGGAGGGCC
GCCCGATCGAGTGACAACGAGACGCCGGCCGGCAGCAGATTG
CTGTCGTTGCCGATGGTCGAGAGAGAGAGNNNNNNNNNNTCGTGTTCGT
CAGCGAGAGCCATTTTCGTTCGTTGGTTCGTTTGATTTGTTTTCCATTCTA
TTTTTCATCTGCAATGGCGATGATCTTGCAAAGCTGCATTGGAGGGAGAGAGGGAG
ACGATAGCGTTATGGATAGGGATTATTTAGCCGCCGTGCGCCCGTGCGTGCGCGTGC
TTAACCATTGCCTTGCCTCGTGATTAAAATTCTGCCATTTTGCACACATCCTTGCCT
GCTGGGTGCTGGCTGCTGCTACAGATGGTAGCTAGCTAGTACAGTTCCTGTAAAGTT
AACAAAAGCTGGCGCGGAGCTAGCCGCAGCCAACAAATAATGCTCGGGGCACAGG
CAGTTGCACCGGTGGTCCGTCGTCGCCCGACGACGGTCCCGGTCCCGGCGGCGGGG
TGAGACCATGTCGCGAAAAGGAAAAAAGGAAACAGAGAATCGGGCAGAGGCTCAC
ATCAGCGACCTTTTTTCTCTTGGACTGCGATGCCGTGCTCTTGCATCAGCTTGGGTCT
CCCAAACAGACAGAACCGTTGGTTTCCGCCTTTCAGGGGTGGCGGCGCCATGGCGG
CGACCCGTCTTCCCTTTTGCTGGTTGCCTATTATATGCATGGCGGCCGCAACGGATTC
GATAGGGATGGACTGCAGTGAATCACTCAAGCAAACGGGATGATATGACGACATAC
AATTTAATAAAAAAAATATATAAGAGAGTTTTATGAAAAATTAAATTGTTTTACGAG
GATGAAACTCTTGATAGACTATTTTCTAAATAAATAAAATATTGATATGGCAACCTT
GAAAACAATGTGATAAAATACCTATTAAGGCNCCGTTTGGTTTGATTGACTAAAGAT
TAGTCCATCCATTTTAGTCTCATTTAGTTCCTAAATTGTCAAACAGTGGAACTAAAAC
AGAGACTAAACTGTTTTAGNNTCTANACCATNNNNNNNNNNNNNNNNNNNNNNNN
NNNNNNATAAATTTCACTTTTTGGTCCTTCTTTATTTCAGTTGCACTAATGGAGGGAG
AGTGCTAAGTAGTATTTTAGTGCTCTTATAATTCATTTAATATGTTTTGAATAGTTTT

AGTCCCTAGAACCAAATAGGATATGGACTAAACTTTAGTCTCCTAACTAAACTTTAG
TCCCTCGACTAAAGGAACCAAACGGGGCATAATAATAGCCTTACCTTAATCTTAGTC
TATTCCCCGCCCTATGTCTTTGTGCCTCGCTCTTGCTCTATGCTCTTCCACTCGCTCCA
CCTCAGTCTCCNNNNNNNCACTCTCTTTGTTGCCCTCCTCAAGTCCAATGAGTCATCT
CCATCGACCACGTCTCCGGTACTCCAAATATTAGAATTACACCCCTCCCTAATCTCT
GTTTCTTTTATCATCTCACCTCTTCTTCGAAACACGTTACCCATCCTCGACATCTATAT
GTTTGACCTCTAAGGGAAAGCAAAGAAAAACTCATCTAGACATATTCTGTATTCTCT
CTATTGCAGGTTCATTCAAGACGTCCGCGGGTGTTCCCACTTTCCATAAAAATATGG
GGCAATATAGTGGGAACAACTCTGAGGCCTGGTGCATAGTTAGAAGTATACCTTCCC
AAAGGGCTTCACACCAGTATAGGTACAAGCGACAAAGAAGTGGAGGAACGAGGGG
GCCAAAGCCACTACATCAATGAAAAGCTTCATAGAGGTAGGTAAAGGCTGAGAAA
GCTAGGATGGCTTTGGGCGTGAGATACACAGGATTGAGCCCATAGTATTCAAGAAT
GCCACGAGAGAAACGAAAAGTGGGAAGTGGACCCCAGAAAGTAGGCATACGTAG
AAGATCACGTACTCACCATCATCTTCCCATGAGAATAGAATCCAGGAAATGACTAG
AGATTACAATTGAGATTGATTTGGCACCGGAAAGCTTCATCTTCTCACATGCAAGAT
CAAATCAATAGTTAAATTGGGGACTTTGTTCATGAGAATGACAAGGGTGAGATTCTT
GATCTTACACTTGTGTGAGAGAGTGGAAATGGAGATTCACTTCATCTTTTCTTCAAC
TAAGCTTGATCTTGTCCTTGATTTTAGCTCCACTTCCCTCTTCTCCATAACTCACTTCT
TGTTCTTCGTTTTTCAAAGAGAATGAGGAAGTGATGAGAGTGAGAGAGTGAGAGGT
GTGGGGAGAGACAAAGTGATTTGAAGATGCTAACTCGGGCTAACTGGTGGGGCCTA
TGGGTGTGTATAAGAGAGCACTCATCCAATGCATGCTTGACACTTCATGTCATGGTA
ATTGATTCTGCCATGGTAACCGGTCAAGTGGGGTCTACCATGTTCCATGGAACTGTC
TGAGAAATAGGTTTAGATAGTCTAAGAAAACACTAGAAATGCTATTTTCTTATTTA
AGATACATGATTGTGAACCAATGTTAACCATTACTTGCACAGATTAGCAAATTGCCA
TTTGAGTTTGGAAGATCGCCTTTCTACTTGATTTATTTGGATCTTGATCCAAATAAGT
AGGTTGAGTTGATTTAAGCGACCTTAATGAGTATAAACGTTGCATGAATAAATAACT
CAAGTTGATACTTCGAAGAAGTTTCAGGTGGTAGCTCGTAGGCCTCGTCCTCTAATA
ACTTACCCATCTCTTACCTTATCCTTCACCTTCAATATACGAATAGTGCAAAATAGTG
TTTTGAATGACCTAACCTGCTAGATATGTTTAAACGTTGGTGGTACAATTCTACAAC
GCAGCAATAGAGATGGTCAAACGGGCTGCCCAACTCGGACTTGTTGAAACCTGACC
CGGTTTGGTCCCGTCCGGAAAGCACG

The invention claimed is:

1. A method of identifying a corn plant or corn germplasm comprising an enhanced sugary gene locus, said method comprising:
   a) detecting in an amplification reaction, in said plant or germplasm genomic DNA, a deletion located on maize chromosome 2 comprising SEQ ID NO: 4; and
   b) identifying a corn plant or corn germplasm comprising the enhanced sugary gene locus.

2. A method of producing a corn plant that produces kernels with enhanced sugary trait, said method comprising:
   a) detecting in an amplification reaction, in corn germplasm genomic DNA that is homozygous for the sugary (su1) mutant allele, the presence of a homozygous deletion located on maize chromosome 2 comprising SEQ ID NO: 4; and
   b) producing a plant from said corn germplasm, thereby producing a corn plant with enhanced sugary trait.

3. The method of claim 1, wherein the deletion comprises nucleotides from about position 10,028 to about position 10,642 of the nucleotide sequence of SEQ ID NO:6.

4. The method of claim 1, wherein detecting the deletion comprises amplifying a region of the corn genome with a primer pair comprising a first oligonucleotide that hybridizes to the nucleotide sequence of SEQ ID NO:6 at a site 5' to the location of the deletion at about position 10,028 and a second oligonucleotide that hybridizes to the nucleotide sequence of SEQ ID NO:6 at a site 3' to the location of the deletion at about position 10,642 to produce an amplification product, wherein an amplification product that differs in base pair size from an amplification product of a control not comprising said deletion.

5. The method of claim 1, wherein detecting said deletion comprises amplifying a region of the corn genome with a primer pair comprising a first oligonucleotide comprising the nucleotide sequence of SEQ ID NO:1 (forward primer) and a second oligonucleotide comprising the nucleotide sequence of SEQ ID NO:3 (reverse primer) to produce an amplification product, wherein an amplification product of about 170 base pairs detects the deletion.

6. A method of selecting a corn plant or corn germplasm comprising an enhanced sugary gene locus, said method comprising:
   a) crossing a first corn plant or corn germplasm with a second corn plant or corn germplasm to produce progeny, wherein the first corn plant or corn germplasm comprises a deletion located on maize chromosome 2 comprising SEQ ID NO: 4,
   b) detecting in an amplification reaction, in genomic DNA from one or more of said progeny, the presence of said deletion; and
   c) selecting from said progeny of b) a corn plant or corn germplasm that comprises said deletion, thereby selecting a corn plant or corn germplasm comprising the enhanced sugary gene locus.

7. A method of introgressing an enhanced sugary gene locus into a corn plant having a genetic background lacking said gene locus, said method comprising:
   a) crossing a donor comprising said gene locus with a recurrent parent that lacks said gene locus to produce progeny; and
   b) repeatedly backcrossing progeny comprising said gene locus with the recurrent parent, wherein said progeny are identified by detecting the presence in an amplification reaction, in their genomic DNA, of a deletion comprising SEQ ID NO: 4 located on maize chromosome 2, thereby producing a corn plant comprising an enhanced sugary gene locus, and thereby introgressing said gene locus into a corn plant having a genetic background lacking said gene locus.

8. The method of claim 7, wherein the genome of the corn plant comprising said enhanced sugary gene locus is at least 95% identical to that of a recurrent parent.

9. The method of claim 1, wherein the deletion is a 615 base-pair deletion consisting of the nucleotide sequence of SEQ ID NO: 4.

10. The method of claim 1, wherein the deletion can be identified in an amplification reaction with a primer pair comprising a first oligonucleotide comprising the nucleotide sequence of SEQ ID NO:1 (forward primer) and a second oligonucleotide comprising the nucleotide sequence of SEQ ID NO:3 (reverse primer) to produce an amplification product, wherein an amplification product of about 170 base pairs detects the deletion.

11. The method of claim 1, wherein said detecting comprises detecting a homozygous deletion located on maize chromosome 2 comprising SEQ ID NO: 4.

* * * * *

SEQUENCE LISTING

```
<160> NUMBER OF SEQ ID NOS: 6

<210> SEQ ID NO 1
<211> LENGTH: 21
<212> TYPE: DNA
<213> ORGANISM: Artificial
<220> FEATURE:
<223> OTHER INFORMATION: PCR primer

<400> SEQUENCE: 1
gcacgtcaga cggagagata g                                                   21

<210> SEQ ID NO 2
<211> LENGTH: 19
<212> TYPE: DNA
<213> ORGANISM: Artificial
<220> FEATURE:
<223> OTHER INFORMATION: PCR primer

<400> SEQUENCE: 2
cgcccgatcg agtgacaac                                                      19

<210> SEQ ID NO 3
<211> LENGTH: 21
<212> TYPE: DNA
<213> ORGANISM: Artificial
<220> FEATURE:
<223> OTHER INFORMATION: PCR primer

<400> SEQUENCE: 3
gtgttcgtca gcgagagcca t                                                   21

<210> SEQ ID NO 4
<211> LENGTH: 615
<212> TYPE: DNA
<213> ORGANISM: Zea mays

<400> SEQUENCE: 4
gtgcacaccg tggagtggac ggcggaggag cgctctctcg atgatccggc cagcgccgtg         60
ggtgggcgcc gggcaccgcg ggcggggcgg cgaggcgggc gcctgcaccg agagcctcgg        120
ctccgagagt ggcgacgtcg gctgcgacgc cgccgagatc gaccagttct tcccgccggc        180
gccggctgct ggcggcccgg acgacgccgg cgcagagccc tgcattccgg acctggcggc        240
ggcggcggcg gcagggaaaa ggcggcgcgg gggcttcccc cgccgatgc cgcgcgcgtc         300 ggggccgctg ttcctgcgcg cggagcgccg cggcggccgc ctcatcctca ccgaggtgcg        360
cgccgacgag cgtgagcgcc gcgttgtgtt ccgcgccgag cgcgacgcg gacgcctccg         420 cctgcgcttc gccaacgacg gcgacggccc cgaggcggca ggtggtggtg gcggcgccgg        480
cggtggaggc ggggagcttt gtcaggtggc cgccggccgg aggggcgtgc aggtcggcgc        540
ggtcatgatg ggggctatct gaaggagggc cgcccgatcg agtgacaacg agacgccggc        600
cggcagcaga ttgct                                                         615

<210> SEQ ID NO 5
<211> LENGTH: 71
<212> TYPE: DNA
<213> ORGANISM: Artificial
<220> FEATURE:
<223> OTHER INFORMATION: Deduced deletion sequence

<400> SEQUENCE: 5
ggccggcagt ggcctagctt gttccattca tccactcagc cggtcgttgc cgatggtcga         60
```

-continued gagagagaga g					71

<210> SEQ ID NO 6
<211> LENGTH: 13500
<212> TYPE: DNA
<213> ORGANISM: Zea mays
<220> FEATURE:
<221> NAME/KEY: misc_feature
<222> LOCATION: (10672)..(10681)
<223> OTHER INFORMATION: n is a, c, g, or t
<220> FEATURE:
<221> NAME/KEY: misc_feature
<222> LOCATION: (11510)..(11510)
<223> OTHER INFORMATION: n is a, c, g, or t
<220> FEATURE:
<221> NAME/KEY: misc_feature
<222> LOCATION: (11613)..(11614)
<223> OTHER INFORMATION: n is a, c, g, or t
<220> FEATURE:
<221> NAME/KEY: misc_feature
<222> LOCATION: (11619)..(11619)
<223> OTHER INFORMATION: n is a, c, g, or t
<220> FEATURE:
<221> NAME/KEY: misc_feature
<222> LOCATION: (11625)..(11654)
<223> OTHER INFORMATION: n is a, c, g, or t
<220> FEATURE:
<221> NAME/KEY: misc_feature
<222> LOCATION: (11949)..(11955)
<223> OTHER INFORMATION: n is a, c, g, or t

<400> SEQUENCE: 6

```
aatactaaaa aaacacagaa agtatactca atagttggca tcagaaaata aataaagatg      60
acaataagaa taccacaatc taccctgact gatctacctg gccagagcag aacggcccaa     120
ctcagatgcc ttttttgtaa tcttcatgtg ctcctaaaag agtccatata tattctagaa     180
gtaattttt tttgaaataa aagttactgt aggggggcta cagtatttta ttgcttaagg     240
aaaaaaggg gtatagatac agaagggtaa gtacagaaag gaaaatgaaa gttacagcac     300
agaaagctga agccaggttt taattttatc tcctattact ggcttaactc gatgacatag     360
aaggttcatt tctgatttga acatatctcg acaaccttcc accgtgggcg gaatctcaat     420
gaacacccaa ttatttctgc attttcagat gccccaggtc aataagatta tagcttcaag     480
tttccagggg acttgccaac gtcttctgat tctcaaaatg gttgtgaata agtcagcaga     540
acgtgatgga gagattccta ccaaggacca acatctccta gcaaaattgc atctgaaaaa     600
aagatgagtg gccgtctctt caacttggag aatacaattg tcacaggagt atgaatccag     660
taacatagct cgctgcctta gaaaagctct ggtattaaat ctgtccttaa gtagcagcca     720
aaaaaacacc ttgtgcttgg gttgacattt ggatttccat agccaagtga agatgagatg     780
tgtccactgg ttgcccatca aatgagaata aatcttttgc gaggaaaata agctagaaga     840
agtagagcag ctccatttgt ctctctgatt attatgtggg agattatcca agcaatcatt     900
caactcttga agtataaaaa aggcttcaac ggacaacggt gcatgaaaca tttcttgggc     960
atcaaccaat cgtgcttgta ggacggtgat gtctttgcat gcagcgaagg accaaagttc    1020
tggatactgt gttgatttgg aaataccatc ccagttatca tgccaaagga gtgttgatct    1080
tccatctcca atttccaccc tagcaattct cttaaatggt tcaagcgttt taaggacatc    1140
tcgccaccaa aaaaccaact ggtttatccg agggcagaga gtgactgtaa tgattggtcc    1200
atacaatatt gacccatggg atgtcagctc tattgaagaa tttatgaaga ttttttcatga    1260
gtagggctct attttgtaaa gccaaattaa ttacacccaa tcccccctaa aattttggct    1320
```

-continued

```
tgcaaaccga attccaagca actagagggg gtttcttagc atttaaatca acacctctcc    1380
aaaggcaatg ccttctgagt ctgtcattat gcttgatcac cgttttgggg agcttaaggg    1440
tgcacatgta gtatgttgga agagaggaga aggctgcatt aaccatttgg agccttccag    1500
cctgtgataa aagatggag gttgacgcca gtcttttttc aattttctgg ataaggggga    1560
gaaaagcacc caagttgggt ctctgaagac ccaagggaag ccctaagtaa gtaaaggcat    1620
tgatccaatt ttgcaatgaa atgtatttgc aaggatctcc attttctggt ccgtgacatt    1680
gatgggataa atgctggatt tatggtaatt cacatgaagc ccagtggagt cagcaaaaga    1740
attgagcatt gcttttaaga agaaaagttg tctagggcag acttccatta tgagaatagt    1800
atcgtcggca tattggatga tagggaaatc cggaccacaa ttgtttggta agggaagacg    1860
aagaatgcca ccttcacaag ctttgttgac aatagactgc agaagatcag ctgcaagaac    1920
aaaagaagc ggtgacaaag gatcaccttg tctaacaccg tgtctgcagt gaaatctttt    1980
cctagggact ccattcaaaa gaacttgtga agaaccggag ccaagaatca taaaaaccca    2040
gtggatccac ttatcaccga accccttgtg cctcaagatc tccataagag ctgcatgctc    2100
caatttatca aatgtctttt caaaatcaag ctttaaaatg accatttcct ttctggattt    2160
gtggcaaagg gaaatatatt caaaagccca tgctaagcaa tcctggatcg atctatcctt    2220
gatgaaacca tattgattct gatgaactag ctttgtgatc actggttgta aatgattggc    2280
taagattttt gttagtactt tgacactcgt gttaaggagg gagatgggtc tataatcacc    2340
aactgaatcc ggagagctat ttttgggaat gagagtcaca tatgacccat taatgctatg    2400
catgcagaga gatccttcaa aaaaattgtt gaaaagatca tagaaatcag gggcaatcac    2460
cggccagcat cttttaacaa agtctgtatt aaagccatct ggacctggcg atttatttga    2520
tggcagacaa gcaatgattt gatcaatctc aagacaagag aaagggtgtt caagctctga    2580
caaattatca atcggctgaa tcaaagcaga taagttgaaa accatggaat tttgtttcat    2640
cttgcttctg cttataaaca atgaaaaagc aatttggtac aggcgctaaa cggaaaggat    2700
ttcggaagat aagcattgct ttgtatgtag aactttcatt ttgacacttt tttttaccga    2760
ggtagtttac aaaatttaaa ttttgaattt gatatactta gattcaattt ttgagaaccg    2820
aaatgagttc aaataaaaaa attgtcaact acaaagttcc ataacttta gagatctata    2880
acttttattt tagtggtttt gtcataggag gtcgtttgaa aaactcgaaa aattaaggat    2940
aaaaatgatt ttagtggcat gtccttaaga aaccaggttt tttaaggaa ccgactgtag    3000
atctctagtg gcggttttct taaggaatcg gcactaaaaa taacacagac ggttggtaac    3060
cgaatccatc tgtacaaata tatcgctccg caggctttga gccttttttct actagtgtgc    3120
cctaccatga atgaaatcaa attttcagga aaaaaataca atacattact tactccatgg    3180
aagtaggctg gttctcatgg gcctattttg agcttctcct tttgggtggg cctaattggt    3240
ggaaacattt tatgggctag gctaacagca cgctctgaat aacacaggtg gattcttcgt    3300
tgagggatgc atcttcattc tcgtccacgc ggagagaaaa aatctttata tgtttgtctc    3360
cactaacatt tatgagaaag cattttcctc gcatcattaa acatgccggg caatcaatat    3420
ttagagacaa atgtaaatta actactagtc ggttgctcgt acattgcaac ggcttacaac    3480
aatacacatg taaactatcc acaaaaaatc aagatttttt attgattgtc tccgctctcc    3540
gtataatatt ttttcgattt ggctaactaa tgttattgtt tactccatcc aatatgtatt    3600
ggtacaacac gatcaatgaa gtgagcgatt agaagagagt tcacaacgac tgactgaacg    3660
aatagaaatt ataaaatggt ataattccac catacagaga ccaaataaga caaagtttgt    3720
```

```
gagctcaagt tctaaaata agtcatatga actcaaactt ataaaaaga tagatcaaaa    3780
tatggagtga ttgctaaaat aagacatcaa taaaatctgg atgtgctcga tataaattat    3840
gctacttcgt agcaattact aacgtttaaa atcaacaaat aacctttcat tttactgtta    3900
gtgtgacaaa tcattgttgc tccatccaat gcagcaacct caaacaccat ttagtctact    3960
gcgtcaatgt ggtcttagaa acgacctaat gcttgcaaga gccaagaaag tcgtgtcatg    4020
cttgggttgt agcctcggct cgcagtgttg atccgtccca acatgattat atatatattt    4080
ttacgaaaaa cgtatataca tatataaaat ttatattcaa tattaaaaac atttgagtac    4140
gatgttctac tgattagaca gcttcaccca gtgtctctcg cccttcttcc atcaggacat    4200
ggtttcgaac cccacctcct gcactgattt aatcaaatgg gccgacgggc tggcccgaca    4260
caattaacag accggcatga cgtacctggg ccagagttgt ggcccacgag cgtctggccc    4320
gtgttgggcc accgtttagc catctataga tgtggagcgg gttaatttga ataactgag    4380
aggttatttg taaaaaaatg atgtgggacg accgttgaaa ctggtgcttt aagtatagta    4440
tagatatcaa acaaataaaa cttaaaatta caagatatag ctactttaag ctttactttg    4500
ctatttatat taggctagta ttgaggtttt tagtagagtt ttagcatgtc aaggaactat    4560
aatttagatc aacggaagtt cgtgagactg agtatgtgtg gaaccagggg acatgaatag    4620
ttctctatcc ctgtctccaa gaactcgtca cggactaact ttccttgttt tgatcctgtg    4680
gggattaaat tacctccatc ctcattccct aatagctaga agaatttctc gcgtgaaatc    4740
agaaatcggg tccattattg ttacccaaag tagacattgg ggataaacat ttatcagcag    4800
cccaggttat gcatgcctgg ttccggagga tagacatgca tgagtggagt ggccgtttcc    4860
atctatctat cggaacggaa acgatacatt gggatgtggt cgcgagataa agaatggga    4920
gatctccagc agccagcact gcagcatggt atagggtcgt cggccggaga accagccaac    4980
cacggccaat gcaaagctag ctgtcacttt ggcaacttgc cgccaaaatg caaaccgata    5040
ccatgcatgt ccatatatga tatactcctg tggctggtta gtcacaatgg taggcatcca    5100
tggccttgag ttttccgaga actagagcca aactcaaact taatcaggac cattggtaac    5160
atataagcgt ccatctcctt tttgataaag gaagctttat taatcttaaa cagttacatc    5220
aagatgatac aatagaacta agattactcc tagtctctac acactaagtg tacatagcca    5280
aacaaaagag aggaaagaaa aaaagaaaa gaaacaaaaa gagaaacaaa cttgtcctaa    5340
agcgagctat cacacacaac agtcttcacg gcaaccaata accagacaaa gctagattca    5400
agattgaggc actccataag caacgtcttc aggaagaaca cggcatataa gagcgtcgcc    5460
attgcgatga cccaaccaac aaaggccaga tcaaaggttt tcacctaaga gaaaatgacc    5520
ctcggtactt cagacaatgc cttcatcaag gtcgatgccc ggcataacca actaagatta    5580
ggcctagaga tttcactcca aagtcgacga gcccaacacc catatgttcc accaaatcaa    5640
agaacatcag tcttgtctcc accttctttc catgctcatg ctgacatacc accaaatctt    5700
ggctaatatc aaacggccat aaactctgaa acaacatcta attttagata gacattccta    5760
tgaagacaga gtcgcaaact agccaatagg cacacgaaca cagtccgtag cttgcatcta    5820
aaaatagaat gtgtcgctcg agcaaaaatg accgtcacaa aattattatg taatataagc    5880
cagagtcgga cagaacgacc actgaataga gctaagtgtt gtctccaaag ttgtccaggc    5940
cgcctctcca aagtcaatca ctttatatag acgttttttt agaaccacca gatgtaggga    6000
tcagtaaaaa tatttctttt tataggcggt taattaagaa gcgtcagtga aaattgattt    6060
```

-continued

```
gcactggcgg ctcagttaaa acaatcaccg gtacaaatcg attttcacta gcggtagact    6120
taagaaaacc acatgtgcaa atcttttcta gtataaattg ggttttaaaa acagcaaaaa    6180
gtgggttttt aaaaacagca aaaatatttt tatttggaga ggctccactc gcccgtcttc    6240
gtcaaagccg aattcgtgtg ctacgcagct ccgtaaaagc cataagccat ggtattttc     6300 gcgcaaaatt catgcactac gcagcccatg gctctcgaat ccgcaacaac ctcaccgttg    6360
tgcataacct cgtctacaac tccacacatc gcttacttgt ctctaaatta cagttttgtt    6420
gtgcacatat tagaacatac cgagtataaa ttgattgttt caggttgtaa acaaattcag    6480
aaggttatca actacaaaat ttaataattt tttaagttct acaacttatt ggtactttt     6540 tcattcgagg ttgtttgtaa aatttgtatt ttaaaattta tccaatttag atgcaatttt    6600
gatagcccaa atgactttaa atgaaaaagt tatcaactac aaagtttcgt aacttttaga    6660
aatctataaa ttttattttg gtggtgtttt catacgtggt catttgaaaa aaactcaaaa    6720
acttgatttc aaatgatttc tacatgcggt tccttaaaaa ctgtcactag aaatacacga    6780
tttatattgg caattttctt aaggaactgt cagtacaaat atgatttcta ctggcggttt    6840
tattaagaaa cccgcctata gaaaatgcac gatttctact agtgttttct taagaaaacc    6900
accagtgaat aagtgttttc actaacagtt cttgagtcga cacaaccaat ttatttacac    6960
tggcgctcga taatcaaaat cgcttgtaaa aattatacct cagcgcatgc atagagattt    7020
gtttgtacta tagtgataat aatcgttccc cgtatgtgaa accaaagtcg gttaggctga    7080
cttctggcat attctaaagt gcttcgttta taaatcgact tttgatgtgg caaccctaga    7140
gatcatattt tggagttgtt ttctaatagg ataagttcaa ccctattaat gcccaaagaa    7200
ggtcatacct tcactaccac caagatctcg atttaaggaa gtttctatgg gggccagcta    7260
ctggggccac tgctcctggg gcaccatgtt caagggcttt atcctggctt tgggaaagat    7320
tagggcttga cactttgggc aacatgatct cagatcattt tgactgaatg tcatatatac    7380
caccaagtcc tcttaagaac catttggaat gtctcttact agaacaattt aagtcatggg    7440
acactcatgc cctagggcac taatgaaaga ttcagatggc aaaggcatac catcccctcg    7500
aggaacttaa tgaaatacac ttaaccgctt gaggccctct actgggcctc aagtacctaa    7560
ggtccttgac ctcacgtaaa atgaatggtg gggccttgat cccctgaggc ccaaggcctc    7620
ttgtgggaac aaggtacttg ttatggctag gtgtaatctt ctccacaaga cagggatgtt    7680
tcctgttcca ccgagcgcac taatgcccca aagcaaggac cctatgttta gggcctacta    7740
acaggtccat aacaccgaca tatcaaataa gtctcttgtg caacattatg tgatgtatgg    7800
cattatagcc tgataggcgc attatcgcca tgatttaggt agttgggtac ttgagaccac    7860
ttttggtatg tgcattgatc ttgtagccac acatgcacat ttcaatgtac cataaagtat    7920
tatcaagtac aaaattctac accggcaaaa caaatatgtc gtacccaacg acattgttcc    7980
taatgttcat agaagagata taacatactt ggcctgcaac aattaattat ggcagccatt    8040
aaagaaggac atctctaaca ctaggctacg acggaaggca tttgttgggg acttgttctc    8100
aaatgctatg agttaagaac aaggcaacat agaaaatgtt aatcgttaaa gcccttcgtc    8160
cttcgaagca tttattcctt taggatataa tggttcctgg acgaaggtta taatgacgt     8220 atttccataa attcatcata cagtgacgaa ggatgaaatg taaggaatat aaaagacagc    8280
ataaacaatt atttattatt attaggtata aacaggaata tcattgaatt acaagtgtac    8340
cttcaactgg aaggagatga tattacaagc gtgacgtaaa aagcgaatgc caagtcagcg    8400
tgaacagtac gggagtactg ttcacctatt tataggcgcg ggacacaacc catacaaaat    8460
```

```
tacattcatg ccctttacag ttgataataa ttctatagta atctgtcgag gtctaaatag    8520
cctttccatc tttaagtcgg tttcactttc tgctgtcacg ccgaagcttc cctgctcaca    8580
ccttcggcgc tgtatcaacc ttcgtattat tctggtctac tgtggtgccg acttgagtcc    8640
gaagatacct gttcacacat tatactccag aaatactgtt aaatcctgtt tttgaggacc    8700
ttcggatgcc gaaggtcccc aacagcattg ctttgaaata tgacttcaca aacaagataa    8760
tattgaagtg gttgggtctt agttggtgag atccaagatc caactgatgt agcctctctc    8820
ctcccttggt ctataaaaga ggagagcaca gtaatgttcg agagatttga tttggaattc    8880
cataagcttt cactcataag ggatttttta ttcttggtta gagactctcg ttcacaatat    8940
ctaaggttag gcataaaggt gaattaggac taatatgcta gaactcctat cataattgat    9000
tggaaaggag gaggtaggat gtcatggcac tcaattaaat cttgagctcg caatcttctt    9060
tacttttgtg ttcacctatc gataagtaac aataggacat aagatattat atgcacgcta    9120
tggcctgaac ctctttaaaa ttgtcagtgt gctagttccc tattagggga tgacaattgg    9180
tatgaaactt gtggtacacg ggttagaaac cggtactcac taaacccgca ctcacatcta    9240
ttaccccgtg acgagtacaa tatatttagg cactcgcacg tcgcacccgc tactctcata    9300
tacaccgagg gcaaataatt agacatattt gacacacaca tagacaacat gtctagtgta    9360
aaaaagatta aattgctaac atgttgacat caaattttgt ccaccagatt catcatctac    9420
agatgagtac aatttcactt gttctgacac tgttttaaac cagcttgggt tattcgtgct    9480
gggctgggca cgagctacta ctccaatgca cgcgttgtgc agctgggcta tgggtgccac    9540
ttgtgcacaa gctgccagcg gcttttcgcc gcggccagcc cagccttgaa ttcctggaga    9600
gcctgcctgg aggcccgtgc ccggctccct cccgctcgct ctcccagtt gcgctccagc    9660
tcagcagctc aggcgtgcgc cgccgccagc gccgcctctc ccataccggg cagcgcgggc    9720
cccacccgct cgctgccccg cacgccagtg accccggacc cgataggcgt gggtgcgtgg    9780
cgtcctcgtc cgccgtcgcc tacagcttag cttctccctc ccgccagctc ggaggcgcca    9840
cgcgccgggc tccgtccgaa acggccggct cgccggttcg gaaactgacg gcggggtggt    9900
acacgtcagc ccagggcccc gcacgtcaga cggagagata ggcatcggcg ggggtatata    9960
aaagcgcctc ctctcgtcct cctcgggccg gcagtggcct agcttgttcc attcatccac   10020
tcagccggtg cacaccgtgg agtggacggc ggaggagcgc tctctcgatg atccggccag   10080
cgccgtgggt gggcgccggg caccgcgggc ggggcggcga ggcgggcgcc tgcaccgaga   10140
gcctcggctc cgagagtggc gacgtcggct gcgacgccgc cgagatcgac cagttcttcc   10200
cgccggcgcc ggctgctggc ggcccggacg acgccggcgc agagccctgc attccggacc   10260
tggcggcggc ggcggcggca gggaaaaggc ggcgcggggc cttcccccg ccgatgccgc   10320
gcgcgtcggg gccgctgttc ctgcgcgcgg agcgccgcgg cggccgcctc atcctcaccg   10380
aggtgcgcgc cgacgagcgt gagcgccgcg ttgtgttccg cgccgagcgc gacggcgac   10440
gcctccgcct gcgcttcgcc aacgacggcg acggcccga ggcggcaggt ggtggtggcg   10500
gcgccggcgg tggaggcggg gagctttgtc aggtggccgc cggccggagg ggcgtgcagg   10560
tcggcgcggt catgatgggg gctatctgaa ggagggccgc ccgatcgagt gacaacgaga   10620
cgccggccgg cagcagattg ctgtcgttgc cgatggtcga gagagagaga gnnnnnnnn    10680
ntcgtgttcg tcagcgagag ccattttcgt tcgttggttc gtttgatttg ttttccattc   10740
tattttcat ctgcaatggc gatgatcttg caaagctgca ttggagggag agagggagac    10800
```

```
gatagcgtta tggataggga ttatttagcc gccgtgcgcc cgtgcgtgcg cgtgcttaac   10860
cattgccttg cctcgtgatt aaaattctgc catttttgca cacatccttg cctgctgggt   10920
gctggctgct gctacagatg gtagctagct agtacagttc ctgtaaagtt aacaaaagct   10980
ggcgcggagc tagccgcagc caacaaataa tgctcgggc acaggcagtt gcaccggtgg   11040
tccgtcgtcg cccgacgacg gtcccggtcc cggcggcggg gtgagaccat gtcgcgaaaa   11100
ggaaaaaagg aaacagagaa tcgggcagag gctcacatca gcgaccttt ttctcttgga   11160 ctgcgatgcc gtgctcttgc atcagcttgg gtctcccaaa cagacagaac cgttggtttc   11220 cgccttcag gggtggcggc gccatggcgg cgacccgtct tcccttttgc tggttgccta   11280
ttatatgcat ggcggccgca acggattcga tagggatgga ctgcagtgaa tcactcaagc   11340
aaacgggatg atatgacgac atacaattta ataaaaaaaa tatataagag agttttatga   11400
aaaattaaat tgttttacga ggatgaaact cttgatagac tattttctaa ataaataaaa   11460
tattgatatg gcaaccttga aaacaatgtg ataaaatacc tattaaggcn ccgtttggtt   11520
tgattgacta aagattagtc catccatttt agtctcattt agttcctaaa ttgtcaaaca   11580
gtggaactaa aacagagact aaactgtttt agnntctana ccatnnnnnn nnnnnnnnnn   11640
nnnnnnnnnn nnnnataaat ttcactttt ggtccttctt tatttcagtt gcactaatgg   11700
agggagagtg ctaagtagta ttttagtgct cttataattc atttaatatg ttttgaatag   11760
ttttagtccc tagaaccaaa taggatatgg actaaacttt agtctcctaa ctaaacttta   11820
gtccctcgac taaaggaacc aaacggggca taataatagc cttaccttaa tcttagtcta   11880
ttccccgccc tatgtctttg tgcctcgctc ttgctctatg ctcttccact cgctccacct   11940
cagtctccnn nnnnncactc tctttgttgc cctcctcaag tccaatgagt catctccatc   12000
gaccacgtct ccggtactcc aaatattaga attcaccccc tccctaatct ctgtttcttt   12060
tatcatctca cctcttcttc gaaacacgtt acccatcctc gacatctata tgtttgacct   12120
ctaagggaaa gcaagaaaaa actcatctag acatattctg tattctctct attgcaggtt   12180
cattcaagac gtccgcgggt gttcccactt tccataaaaa tatggggcaa tatagtggga   12240
acaactctga ggcctggtgc atagttagaa gtataccttc ccaaagggct tcacaccagt   12300
ataggtacaa gcgacaaaga agtggaggaa cgaggggggcc aaagccacta catcaatgaa   12360
aaagcttcat agaggtaggt aaaggctgag aaagctagga tggctttggg cgtgagatac   12420
acaggattga gcccatagta ttcaagaatg ccacgagaga aacgaaaaag tgggaagtgg   12480
accccagaaa gtaggcatac gtagaagatc acgtactcac catcatcttc ccatgagaat   12540
agaatccagg aaatgactag agattacaat tgagattgat ttggcaccgg aaagcttcat   12600
cttctcacat gcaagatcaa atcaatagtt aaattgggga ctttgttcat gagaatgaca   12660
agggtgagat tcttgatctt acacttgtgt gagagagtgg aaatggagat tcacttcatc   12720
tttttcttca actaagcttg atcttgtcct tgattttagc tccacttccc tcttctccat   12780
aactcacttc ttgttcttcg ttttcaaag agaatgagga agtgatgaga gtgagagagt   12840
gagaggtgtg gggagagaca aagtgatttg aagatgctaa ctcgggctaa ctggtggggc   12900
ctatgggtgt gtataagaga gcactcatcc aatgcatgct tgacacttca tgtcatggta   12960
attgattctg ccatggtaac cggtcaagtg gggtctacca tgttccatgg aactgtctga   13020
gaaataggtt tagatagtct aagaaaacac tagaaatgct attttctta tttaagatac   13080 atgattgtga accaatgtta accattactt gcacagatta gcaaattgcc atttgagttt   13140
ggaagatcgc ctttctactt gatttatttg gatcttgatc caaataagta ggttgagttg   13200
```

-continued

```
atttaagcga ccttaatgag tataaacgtt gcatgaataa ataactcaag ttgatacttc   13260
gaagaagttt caggtggtag ctcgtaggcc tcgtcctcta ataacttacc catctcttac   13320
cttatccttc accttcaata tacgaatagt gcaaaatagt gttttgaatg acctaacctg   13380
ctagatatgt ttaaacgttg gtggtacaat tctacaacgc agcaatagag atggtcaaac   13440
gggctgccca actcggactt gttgaaacct gacccggttt ggtcccgtcc ggaaagcacg   13500
```